(12) United States Patent
Sheetrit et al.

(10) Patent No.: US 12,318,394 B2
(45) Date of Patent: Jun. 3, 2025

(54) DEVICES AND METHODS FOR DELIVERING A BIO-ACTIVE AGENT OR BIO-ACTIVE AGENTS

(71) Applicant: EXIMORE LTD., Jerusalem (IL)

(72) Inventors: Eyal Sheetrit, Shoam (IL); Izhar Halahmi, Hod Hasharon (IL); Ishay Attar, Nahsholim (IL)

(73) Assignee: EXIMORE LTD., Jerusalem (IL)

( * ) Notice: Subject to any disclaimer, the term of this patent is extended or adjusted under 35 U.S.C. 154(b) by 958 days.

(21) Appl. No.: 17/078,534

(22) Filed: Oct. 23, 2020

(65) Prior Publication Data
US 2021/0137942 A1  May 13, 2021

Related U.S. Application Data

(62) Division of application No. 16/531,665, filed on Aug. 5, 2019, now abandoned, which is a division of application No. 15/529,474, filed as application No. PCT/IB2015/002345 on Nov. 25, 2015, now Pat. No. 10,471,070.

(60) Provisional application No. 62/084,387, filed on Nov. 25, 2014.

(51) Int. Cl.
| | | |
|---|---|---|
| A61K 31/5377 | (2006.01) | |
| A61K 9/00 | (2006.01) | |
| A61K 31/5575 | (2006.01) | |
| A61K 47/02 | (2006.01) | |
| A61K 47/32 | (2006.01) | |
| A61K 47/34 | (2017.01) | |

(52) U.S. Cl.
CPC ........ *A61K 31/5575* (2013.01); *A61K 9/0051* (2013.01); *A61K 31/5377* (2013.01); *A61K 47/02* (2013.01); *A61K 47/32* (2013.01); *A61K 47/34* (2013.01)

(58) Field of Classification Search
None
See application file for complete search history.

(56) References Cited

U.S. PATENT DOCUMENTS

| | | |
|---|---|---|
| 2008/0181930 A1 | 7/2008 | Rodstrom et al. |
| 2009/0306595 A1 | 12/2009 | Shih et al. |
| 2013/0142858 A1 | 6/2013 | Kopczynski et al. |

FOREIGN PATENT DOCUMENTS

| | | |
|---|---|---|
| CN | 101600476 A | 12/2009 |
| WO | 2008094989 A2 | 8/2008 |
| WO | 2011146483 A1 | 11/2011 |
| WO | 2014160828 A1 | 10/2014 |

*Primary Examiner* — Alton N Pryor
(74) *Attorney, Agent, or Firm* — Greenberg Traurig, LLP

(57) ABSTRACT

In some embodiments, the present invention is a composition, including: a bulking agent, where the bulking agent is a kaolin, an absorbent material, where the absorbent material is a fumed silica, a binder, where the binder is an epoxy, and a first active agent, where the first active agent is Latanoprost.

12 Claims, 23 Drawing Sheets

An illustration of the lacrimal duct system of a mammalian eye

An illustration of one of the present medical devices positioned in the lacrimal duct system of a mammalian eye Compact mini dilator and mini plug applicator Compact mini dilator and mini plug applicator Peak: Latan

| | Sample Name | | X Value | Date Acquired | A** ****** | Manual | | Calc. Value | % Deviation |
|---|---|---|---|---|---|---|---|---|---|
| 1 | A1 | 65 | 0.481200 | 8/30/2016 3:02:53 PM | 27806 | No | No | 0.653342 | 36.773 |
| 2 | A2 | 65 | 2.400000 | 8/30/2015 3:26:01 PM | 69391 | No | No | 2.675349 | 11.381 |
| 3 | A3 | 67 | 12.000000 | 8/30/2015 3:49:09 PM | 255632 | No | No | 11.957582 | -0.502 |
| 4 | A4 | 68 | 24.050000 | 8/30/2015 4:12:17 PM | 500453 | No | No | 23.681126 | -1.576 |
| 5 | A5 | 69 | 48.120000 | 8/30/2015 4:35:24 PM | 994541 | No | No | 47.767137 | -0.730 |
| 6 | A6 | 70 | 120.300000 | 8/30/2015 4:58:32 PM | 2493853 | No | No | 120.789401 | 0.416 |
| 7 | A7 | 71 | 240.800000 | 8/30/2015 5:21:41 PM | 4949545 | No | No | 240.455452 | -0.050 |

FIGURE 14B

DEVICES AND METHODS FOR DELIVERING A BIO-ACTIVE AGENT OR BIO-ACTIVE AGENTS

RELATED APPLICATIONS

This application is a Divisional of U.S. patent application Ser. No. 16/531,665, filed Aug. 5, 2019, which is a Divisional of U.S. patent application Ser. No. 15/529,474 filed on May 24, 2017, now U.S. Pat. No. 10,471,070, which is a 371 National Entry of International Application No. PCT/IB2015/002345, filed Nov. 25, 2015, which claims the priority of U.S. provisional application U.S. Patent Appln. No. 62/084,387, filed Nov. 25, 2014, which are incorporated herein by reference in their entireties for all purposes

TECHNICAL FIELD

In some embodiments, the instant invention is related to compositions and methods for delivering a bio-active agent or bio-active agents.

BACKGROUND

Glaucoma is the most frequent cause for irreversible and preventable blindness worldwide. About two percent of the population over 40 years of age suffers from glaucoma. The major risk factor and only treatable factor in glaucoma is increased intraocular pressure. While glaucoma is incurable, treatment can slow or arrest the progressive vision loss.

SUMMARY OF INVENTION

In some embodiments, the composition of the present invention is a drug-delivery device comprising: a) a composite comprising the following elements: (i) particles of inert materials, where the inert materials are adsorbed with drug on surface of particles (e.g., drug bound to particles) or inside porosity (e.g., drug housed within pores); (ii) a bulking agent; (iii) an adhesive binder; or any combination thereof, and b) an optional coating on the whole or partial outer surface of the body/core; where the coating is complete/continuous or perforated, e.g., but not limited to, where the coating can be butvar and/or parylene.

In some embodiments, the present invention is a composition, including: a bulking agent including a kaolin and/or a pectin, an absorbent material including a fumed silica, a binder including an epoxy, and a first active agent including Latanoprost. In some embodiments, the first active agent measures between 5-50% by weight (w/w). In some embodiments, the first active agent measures between 5-45% by weight (w/w). In some embodiments, the first active agent measures between 5-40% by weight (w/w). In some embodiments, the first active agent measures between 5-35% by weight (w/w). In some embodiments, the first active agent measures between 5-30% by weight (w/w). In some embodiments, the first active agent measures between 5-25% by weight (w/w). In some embodiments, the first active agent measures between 5-20% by weight (w/w). In some embodiments, the first active agent measures between 5-15% by weight (w/w). In some embodiments, the first active agent measures between 5-10% by weight (w/w). In some embodiments, the first active agent measures between 10-50% by weight (w/w). In some embodiments, the first active agent measures between 15-50% by weight (w/w). In some embodiments, the first active agent measures between 20-50% by weight (w/w). In some embodiments, the first active agent measures between 25-50% by weight (w/w). In some embodiments, the first active agent measures between 30-50% by weight (w/w). In some embodiments, the first active agent measures between 35-50% by weight (w/w). In some embodiments, the first active agent measures between 40-50% by weight (w/w). In some embodiments, the first active agent measures between 45-50% by weight (w/w). In some embodiments, the first active agent measures between 10-45% by weight (w/w). In some embodiments, the first active agent measures between 15-40% by weight (w/w). In some embodiments, the first active agent measures between 20-35% by weight (w/w). In some embodiments, the first active agent measures between 20-30% by weight (w/w). In some embodiments, the compound further includes a second active agent. In some embodiments, the second active agent is Timolol. In some embodiments, the second active agent measures between 5-40% by weight (w/w). In some embodiments, the second active agent measures between 5-35% by weight (w/w). In some embodiments, the second active agent measures between 5-30% by weight (w/w). In some embodiments, the second active agent measures between 5-25% by weight (w/w). In some embodiments, the second active agent measures between 5-20% by weight (w/w). In some embodiments, the second active agent measures between 5-15% by weight (w/w). In some embodiments, the second active agent measures between 5-10% by weight (w/w). In some embodiments, the second active agent measures between 10-40% by weight (w/w). In some embodiments, the second active agent measures between 15-40% by weight (w/w). In some embodiments, the second active agent measures between 20-40% by weight (w/w). In some embodiments, the second active agent measures between 25-40% by weight (w/w). In some embodiments, the second active agent measures between 30-40% by weight (w/w). In some embodiments, the second active agent measures between 35-40% by weight (w/w). In some embodiments, the second active agent measures between 10-35% by weight (w/w). In some embodiments, the second active agent measures between 15-30% by weight (w/w). In some embodiments, the second active agent measures between 20-25% by weight (w/w). In some embodiments, the composition further includes polyurethane. In some embodiments, the composition further includes a parylene coating. In some embodiments, the parylene coating measures between 2-5 micrometers (e.g., but not limited to, 2.1 micrometers, 2.2 micrometers, etc.) in thickness. In some embodiments, the composition includes a butvar coating. In some embodiments, the butvar coating measures between 2-5 micrometers (e.g., but not limited to, 2.1 micrometers, 2.2 micrometers, etc.) in thickness. In some embodiments, the composition is in the form of a punctal plug.

In some embodiments, the present invention is a method, including: administering a composition to an eye of a mammal in need thereof, where the composition releases between 0.5-10 micrograms of a first active agent per day, and where the composition includes: a bulking agent including a kaolin, an absorbent material including a fumed silica, a binder including an epoxy, and the first active agent includes Latanoprost. In some embodiments, the first active agent measures between 5-50% by weight (w/w). In some embodiments, the first active agent measures between 5-45% by weight (w/w). In some embodiments, the first active agent measures between 5-40% by weight (w/w). In some embodiments, the first active agent measures between 5-35% by weight (w/w). In some embodiments, the first active agent measures between 5-30% by weight (w/w). In some embodiments, the first active agent measures between 5-25% by weight (w/w). In some embodiments, the first active agent measures between 5-20% by weight (w/w). In some embodiments, the first active agent measures between 5-15% by weight (w/w). In some embodiments, the first active agent measures between 5-10% by weight (w/w). In some embodiments, the first active agent measures between 10-50% by weight (w/w). In some embodiments, the first active agent measures between 15-50% by weight (w/w). In some embodiments, the first active agent measures between 20-50% by weight (w/w). In some embodiments, the first active agent measures between 25-50% by weight (w/w). In some embodiments, the first active agent measures between 30-50% by weight (w/w). In some embodiments, the first active agent measures between 35-50% by weight (w/w). In some embodiments, the first active agent measures between 40-50% by weight (w/w). In some embodiments, the first active agent measures between 45-50% by weight (w/w). In some embodiments, the first active agent measures between 10-35% by weight (w/w). In some embodiments, the first active agent measures between 10-45% by weight (w/w). In some embodiments, the first active agent measures between 15-40% by weight (w/w). In some embodiments, the first active agent measures between 20-35% by weight (w/w). In some embodiments, the first active agent measures between 25-30% by weight (w/w). In some embodiments, the method includes a second active agent. In some embodiments, the second active agent is Timolol. In some embodiments, the second active agent includes between 5-40% by weight (w/w). In some embodiments, the second active agent measures between 5-35% by weight (w/w). In some embodiments, the second active agent measures between 5-30% by weight (w/w). In some embodiments, the second active agent measures between 5-25% by weight (w/w). In some embodiments, the second active agent measures between 5-20% by weight (w/w). In some embodiments, the second active agent measures between 5-15% by weight (w/w). In some embodiments, the second active agent measures between 5-10% by weight (w/w). In some embodiments, the second active agent measures between 10-40% by weight (w/w). In some embodiments, the second active agent measures between 15-40% by weight (w/w). In some embodiments, the second active agent measures between 20-40% by weight (w/w). In some embodiments, the second active agent measures between 25-40% by weight (w/w). In some embodiments, the second active agent measures between 30-40% by weight (w/w). In some embodiments, the second active agent measures between 35-40% by weight (w/w). In some embodiments, the second active agent measures between 10-35% by weight (w/w). In some embodiments, the second active agent measures between 15-30% by weight (w/w). In some embodiments, the second active agent measures between 20-25% by weight (w/w). In some embodiments, the method includes a parylene coating. In some embodiments, the parylene coating measures between 2-5 micrometers (e.g., but not limited to, 2.1 micrometers, 2.2 micrometers, etc.) in thickness. In some embodiments, the composition includes a butvar coating. In some embodiments, the butvar coating measures between 2-5 micrometers (e.g., but not limited to, 2.1 micrometers, 2.2 micrometers, etc.) in thickness. In some embodiments, the composition is in the form of a punctal plug.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIGS. 13 and 14A-14B illustrate a typical chromatogram of a standard solution.

In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DESCRIPTION OF EXEMPLARY EMBODIMENTS

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Figure 4:
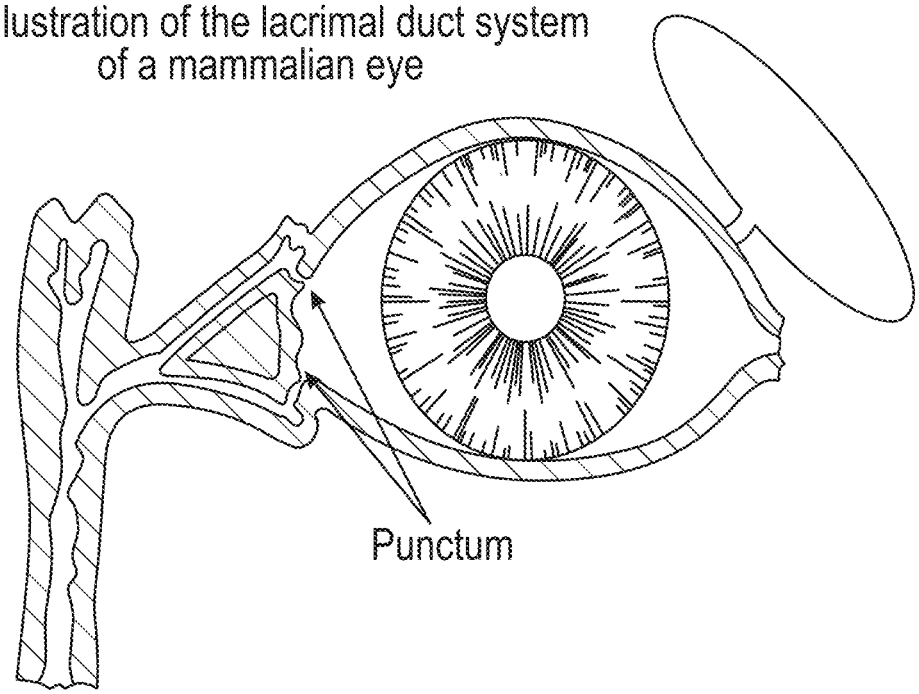
FIGS. 4 and 5 illustrate embodiments of placement of the compositions of the present invention.
Figure 5:
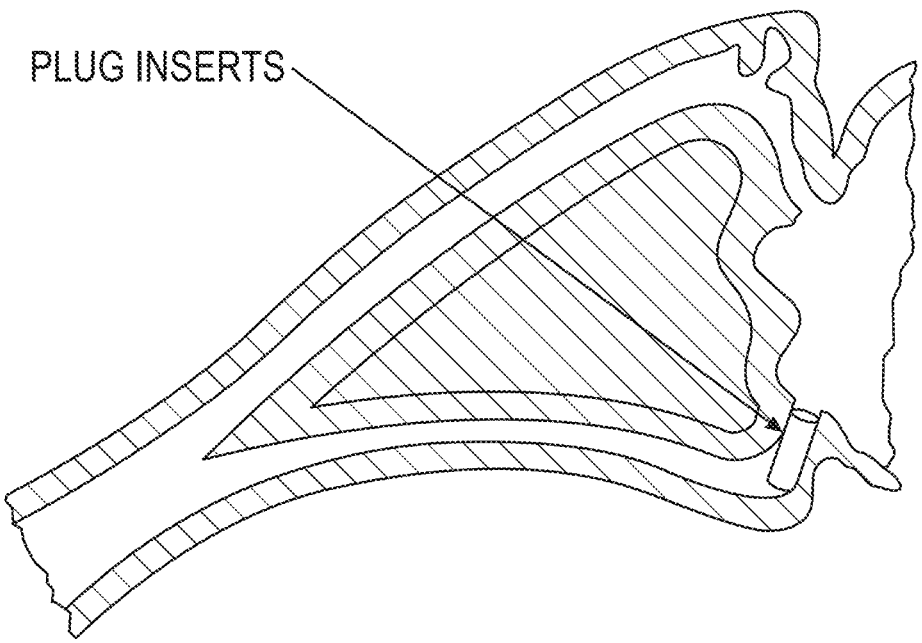
Figure 6:
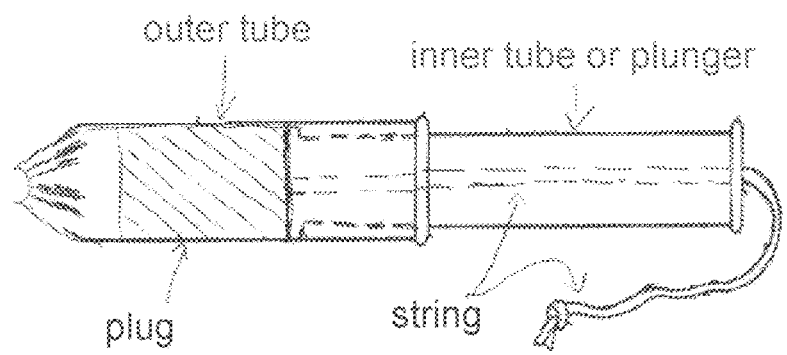
FIGS. 6 and 7 illustrate embodiments of applicators for placing the compositions of the present invention in an eye.

The present invention relates generally to the field of medicine combining drug in a device, for administering a bio-active agent over a prolonged period of time. More particularly, it concerns implantable ocular devices for the sustained delivery of a therapeutic compound to the eye. FIGS. 4-6 illustrate the lacrimal duct system of the human eye and embodiments of the compositions of the present invention placed within the lacrimal duct system of the human eye. In an embodiment, the composition of the present invention is placed in an eye by performing the following steps: (1) hold the applicator (where the ridges are on the tube); (2) insert the applicator (big tube) into the punctum; (3) push the bottom of the small tube completely up inside the big tube (this slides the plug out of the applicator and into the punctum); and (4) gently take out both applicator tubes together.

Figure 7:
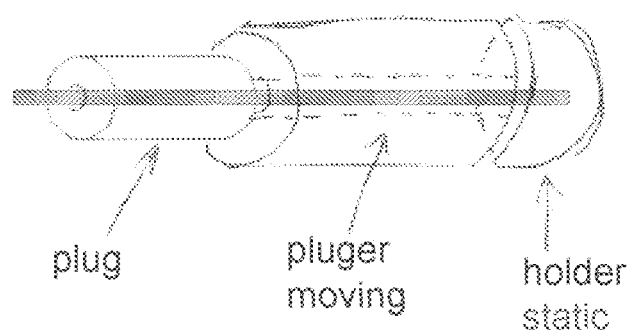

In an embodiment, FIG. 7 illustrates a composition of the present invention. In an embodiment, the composition of the present invention is placed in an eye by performing the following steps: (1) hold the applicator (where the ridges are on the static tube); (2) insert the plug's inserter (metal part) into the punctum; and (3) push the moving plunger completely up with the plug (both the plug and the plunger are moving on the static metal inserter (this slides the plug out of the applicator into the punctum (the plunger remains outside the punctum); gently take out both plunger and holder together.

In some embodiments, the present invention is a composite device that configured to contain and release an amount of drug per volume. In some embodiments, the device is configured to allow multiple drug loading (e.g., but not limited to, 2 drugs, 3 drugs, 4 drugs, 5 drugs, etc.). In some embodiments, the drug molecules are physically bound to the matrix. In some embodiments, a non-metallic coating provides zero-order or near zero-order drug-release kinetics. In some embodiments, a release profile provides zero-order or near zero-order drug-release kinetics at two different rates; initially higher rate at the first several weeks, and thereafter a lower rate.

Figure 8:
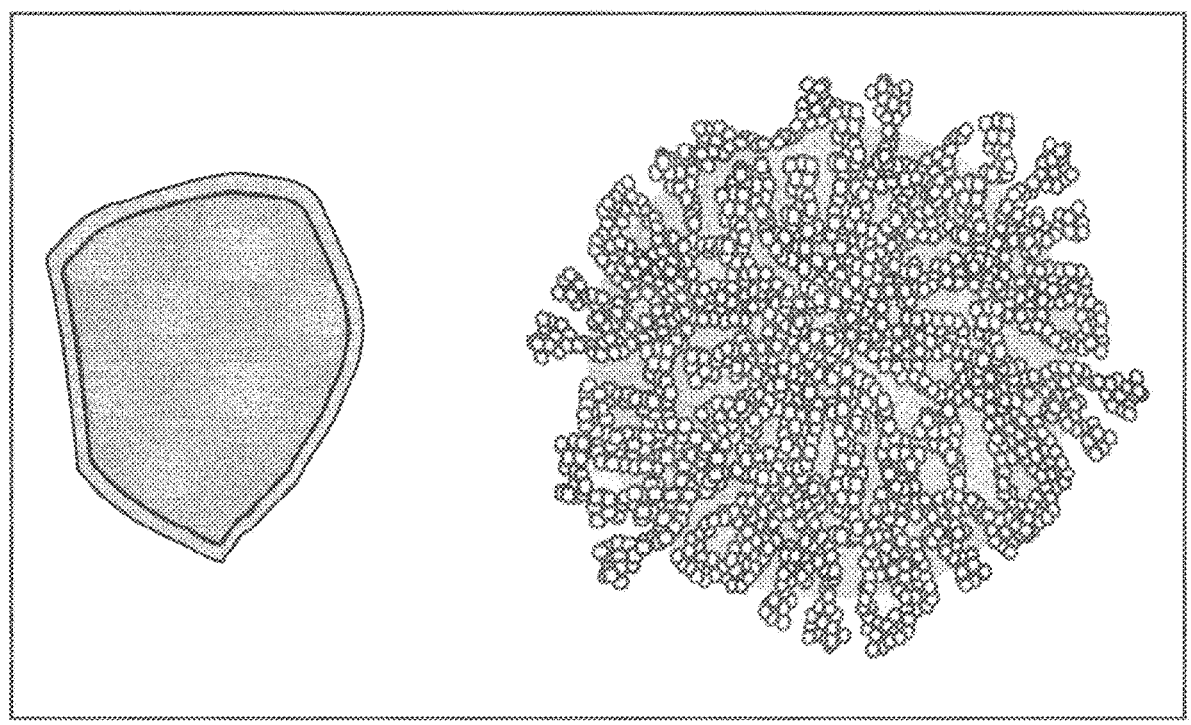
FIG. 8 is a schematic depiction of liquid at the surface of anon-porous particle (left) and of liquid absorbed in the pores of fumed silica (right).
Figure 9:
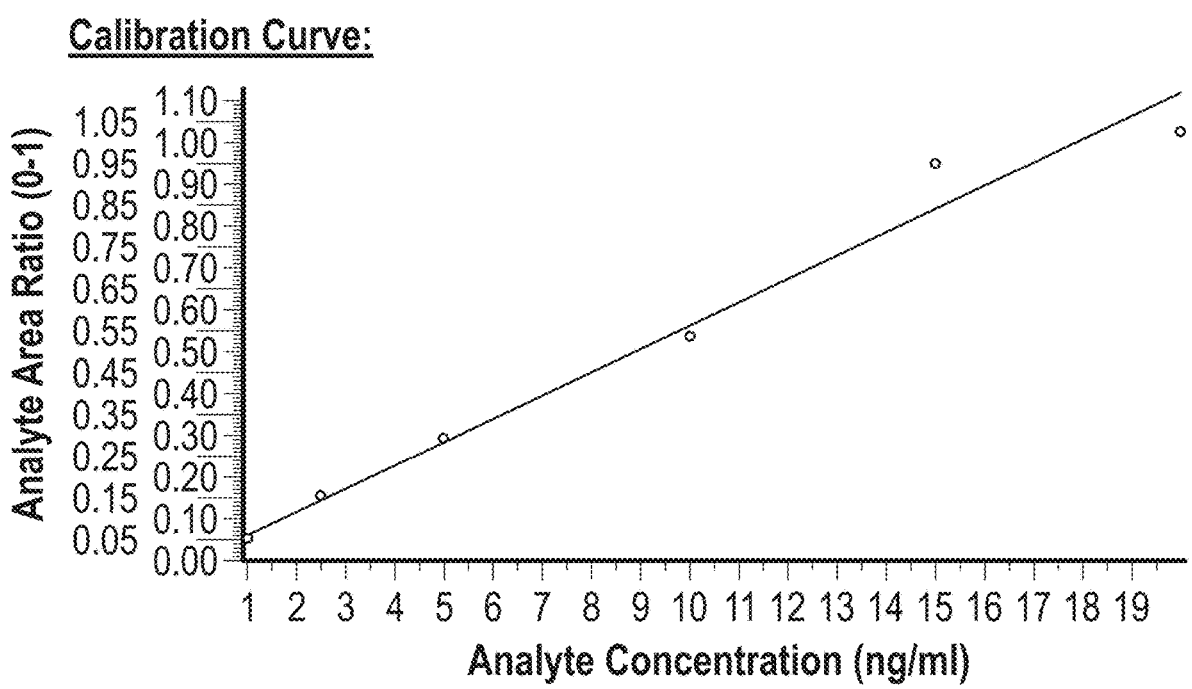
FIG. 9 illustrates a calibration curve of an embodiment of the composition of the present invention.
Figure 10:
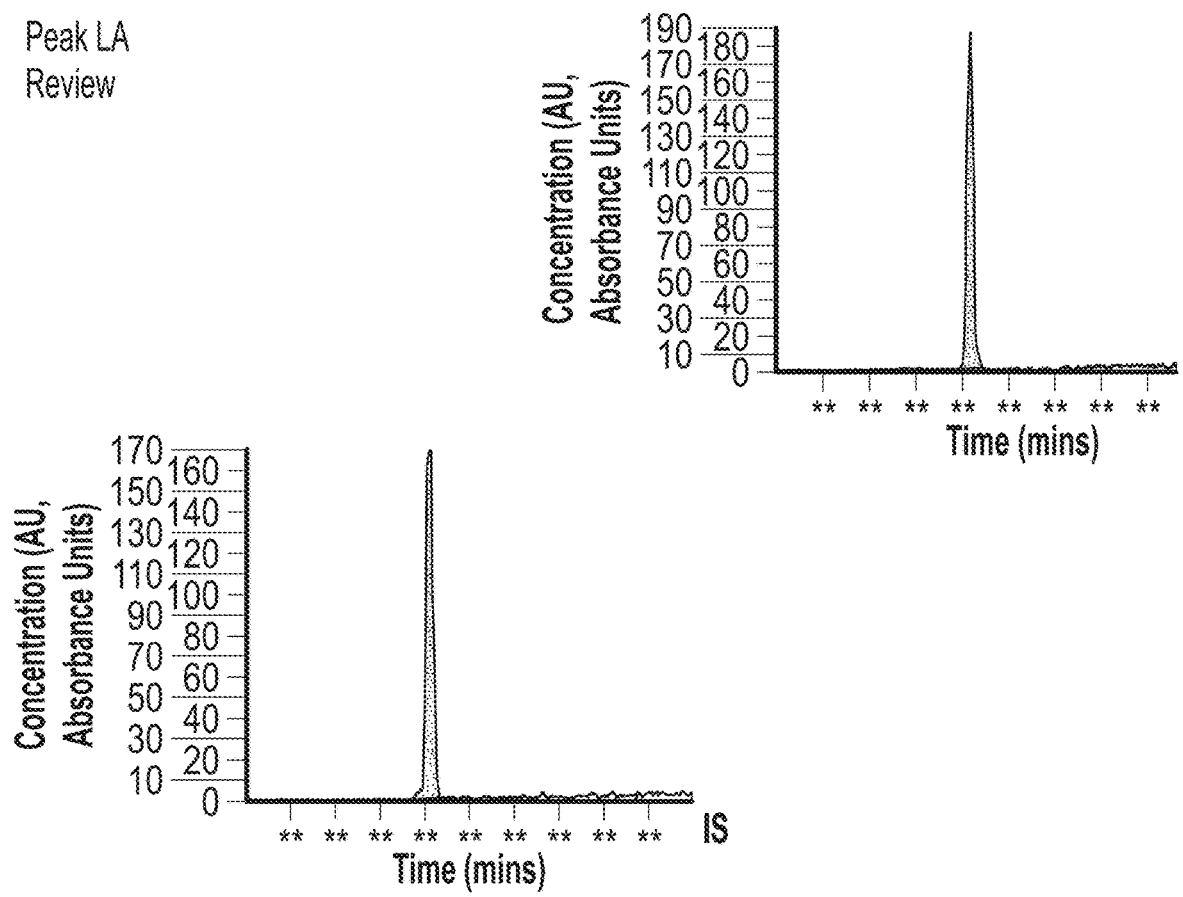
FIG. 10 illustrates a chromatogram of a standard solution.
Figure 11:
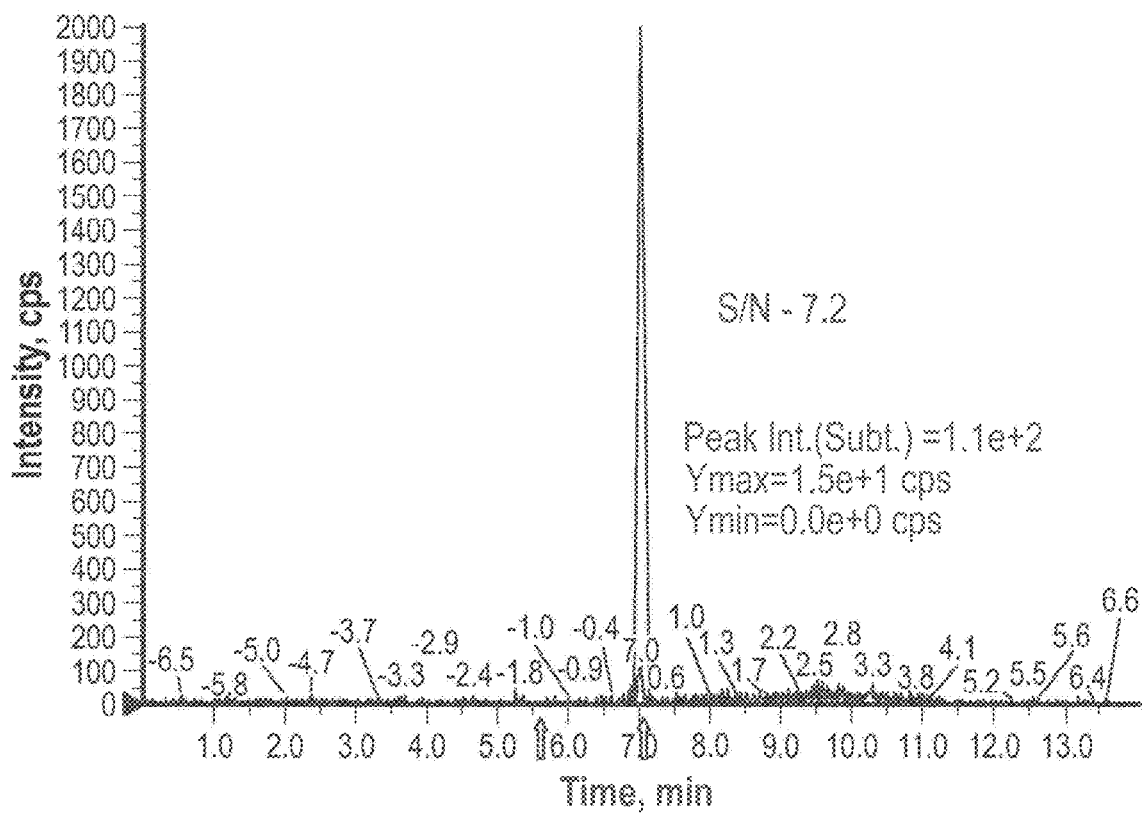
FIG. 11 illustrates a chromatogram of an embodiment of the composition of the present invention.

In some embodiments, the composition of the present invention is a drug-delivery device composite shaped into the desired body/shape; whereas the composite comprising of the following: (1) particles of inert materials, having a porous structure, with an increase surface area and low bulk density. Fumed silica, silica gel, activated carbon, activated alumina or zeolite products offer a porous structure with an interconnected capillary network similar to an open cell sponge. FIG. 8 is a schematic depiction of liquid at the surface of a non-porous particle (left) and of liquid absorbed in the pores of fumed silica (right).

The small diameter of the pores leads to high capillary forces that draw the liquid into the particle. This physical absorption mechanism is independent of the chemical characteristics of the liquid; therefore both polar as well as non-polar liquids can be absorbed. For instance, in Fumed Silica the surface area is 10-600 m2/gr, in silica gel it is around 800 m2/gr. Hence, the finished absorbate can contain between 50-75% of the liquid actives with drug on surface of particles or inside porosity, e.g., but not limited to, fumed silica loaded (i.e., bound) with prostaglandin; (2) a bulking agent e.g., but not limited to, kaolin and/or pectin; (3) an adhesive binder, e.g., but not limited to, ceramic adhesive, e.g., but not limited to, epoxy adhesive; (4) a hydrophobic flexible polymer e.g., but not limited to, PU, or any combination thereof. In some embodiments, the physical mechanism of adsorbing liquid actives is passive.

In some embodiments, the composition of the present invention is a drug-delivery device comprising: a) a composite comprising the following elements: (i) particles of inert materials, where the inert materials are adsorbed with drug on surface of particles (e.g., drug bound to particles) or inside porosity (e.g., drug housed within pores); (ii) a bulking agent; (iii) an adhesive binder; (iv) a hydrophobic flexible polymer; or any combination thereof, and b) an optional coating on the whole or partial outer surface of the body/core; where the coating is complete/continuous or perforated, e.g., but not limited to, where the coating can be butvar and/or parylene.

In some embodiments, the composition of the present invention includes an ophthalmic drug, where the ophthalmic drug is a prostaglandin analog, beta blocker, Alpha agonist, carbonic anhydrase inhibitor, adenosine agonist, Rho Kinase inhibitor or any combination thereof. In some embodiments, the prostaglandin is cloprostenol, fluprostenol, latanoprost, travoprost, unoprostone, Latanoprostene bunod or any combination thereof. In some embodiments, more than one drug (e.g., 2, 3, 4, 5, etc.) is loaded into the matrix to be release independently and in parallel whereas each drug is released according to (a) its natural solubility in the external medium and (b) to the barriers whether by the hydrophobic polymer, the external impermeable barrier or both. In some embodiments, the concentration of the prostaglandin in the matrix is between about 1% to about 20% by weight. In some embodiments, the concentration of the prostaglandin in the matrix is between about 10% to about 17% by weight.

In some embodiments of the composition of the present invention, the concentration of the prostaglandin in the matrix is between about 10% to about 15% by weight. In some embodiments, the concentration of the prostaglandin in the matrix is between about 10% to about 13% by weight. In some embodiments, the concentration of the prostaglandin in the matrix is between about 5% to about 20% by weight. In some embodiments, the concentration of the prostaglandin in the matrix is between about 10% to about 20% by weight. In some embodiments, the concentration of the prostaglandin in the matrix is between about 13% to about 20% by weight. In some embodiments, the concentration of the prostaglandin in the matrix is between about 15% to about 20% by weight.

In some embodiments, the composition of the present invention is a drug-delivery device comprising: a) a composite comprising the following elements: (i) particles of inert materials, where the inert materials are adsorbed with drug on surface of particles (e.g., drug bound to particles) or inside porosity (e.g., drug housed within pores); (ii) a bulking agent; (iii) an adhesive binder; and b) a optional coating on the whole or partial outer surface of the body/core; where the coating is complete/continuous or perforated, e.g., but not limited to, where the coating can be butvar and/or parylene.

In some embodiments, the composition of the present invention includes an ophthalmic drug, where the ophthalmic drug is a prostaglandin analog, beta blocker, Alpha agonist, carbonic anhydrase inhibitor, adenosine agonist, Rho Kinase inhibitor or any combination thereof. In some embodiments, the prostaglandin is cloprostenol, fluprostenol, latanoprost, travoprost, unoprostone, Latanoprostene bunod or any combination thereof. In some embodiments, more than one drug (e.g., 2, 3, 4, 5, etc.) is loaded into the matrix to be release independently and in parallel whereas each drug is released according to (a) its natural solubility in the external medium and (b) to the barriers whether by the composite, the external semi-permeable barrier or both. In some embodiments, the concentration of the prostaglandin in the matrix is between about 1% to about 50% by weight. In some embodiments, the concentration of the prostaglandin in the matrix is between about 30% to about 40% by weight.

In some embodiments of the composition of the present invention, the concentration of the prostaglandin in the matrix is between about 30% to about 40% by weight. In some embodiments, the concentration of the prostaglandin in the matrix is between about 32% to about 38% by weight. In some embodiments, the concentration of the prostaglandin in the matrix is between about 5% to about 40% by weight. In some embodiments, the concentration of the prostaglandin in the matrix is between about 10% to about 40% by weight. In some embodiments, the concentration of the prostaglandin in the matrix is between about 23% to about 40% by weight. In some embodiments, the concentration of the prostaglandin in the matrix is between about 15% to about 40% by weight.

In some embodiments of the composition of the present invention, the parylene coating is between about 0.3 µm to about 20 µm thick. In some embodiments, the parylene coating is between about 0.3 µm to about 10 µm thick. In some embodiments, the parylene coating is between about 0.3 µm to about 5 µm thick. In some embodiments, the parylene coating is between about 0.3 µm to about 3 µm thick. In some embodiments, the parylene coating is between about 0.3 µm to about 1 µm thick. In some embodiments, the parylene coating is between about 1 µm to about 20 µm thick. In some embodiments, the parylene coating is between about 3 µm to about 20 µm thick. In some embodiments, the parylene coating is between about 5 µm to about 20 µm thick. In some embodiments, the parylene coating is between about 10 µm to about 20 µm thick.

In some embodiments of the composition of the present invention, the butvar coating is between about 1 µm to about 20 µm thick. In some embodiments, the butvar coating is between about 5 µm to about 20 µm thick. In some embodiments, the butvar coating is between about 10 µm to about 20 µm thick. In some embodiments, the butvar coating is between about 15 µm to about 20 µm thick. In some embodiments, the butvar coating is between about 1 µm to about 15 µm thick. In some embodiments, the butvar coating is between about 1 µm to about 10 µm thick. In some embodiments, the butvar coating is between about 1 µm to about 5 µm thick. In some embodiments, the butvar coating is between about 5 µm to about 15 µm thick.

In some embodiments of the composition of the present invention, the core/body further comprises a canalicular extension attached to the distal tip portion of the core/body, where the canalicular extension is configured for insertion through the punctual aperture and the punctum and positioning in the lacrimal canaliculus. In some embodiments, the canalicular extension has a length L1 and the body has a length L2, wherein the ratio of the length L1 to the length L2 is between about 2:1 to about 10:1. In some embodiments, the ratio of the length L1 to the length L2 is between about 2:1 to about 8:1. In some embodiments, the ratio of the length L1 to the length L2 is between about 2:1 to about 6:1. In some embodiments, the ratio of the length L1 to the length L2 is between about 2:1 to about 4:1. In some embodiments, the ratio of the length L1 to the length L2 is between about 4:1 to about 10:1. In some embodiments, the ratio of the length L1 to the length L2 is between about 6:1 to about 10:1. In some embodiments, the ratio of the length L1 to the length L2 is between about 8:1 to about 10:1.

In some embodiments of the composition of the present invention, the canalicular extension is configured for positioning in a lacrimal canaliculus and/or a nasolacrimal duct. In some embodiments, a core/body has an outer surface and is configured to be inserted through a punctal aperture and positioned in a punctum or lacrimal canaliculus, wherein the body is a monolithic capsule structure or cylinder shape. In some embodiments, the composition includes a parylene coating or butvar coating covering the outer surface of the body, the parylene coating or butvar coating being substantially impermeable (its surface is impermeable above thicknesses of 1.4 nanometers) to drug (e.g., a prostaglandin); and at least one pore in the parylene coating or butvar coating pore, wherein the amount and/or size of the pore is configured to release the prostaglandin (e.g., but not limited to, Latanoprost) at a therapeutically effective dose for a period of 1 to 360 days (e.g., 1, 2, 3, 4, 5, etc. days). In some embodiments, the period measures between 1 to 180 days. In some embodiments, the period measures between 1 to 120 days. In some embodiments, the period measures between 1 to 60 days. In some embodiments, the period measures between 1 to 30 days. In some embodiments, the period measures between 30 to 180 days. In some embodiments, the period measures between 60 to 180 days. In some embodiments, the period measures between 90 to 180 days. In some embodiments, the period measures between 120 to 180 days. In some embodiments, the period measures between 30 to 120 days. In some embodiments, the period measures between 60 to 90 days.

In some embodiments of the composition of the present invention, the beta-adrenergic receptor antagonists can be timolol, levobunolol (Betagan), betaxolol, or any combination thereof.

In some embodiments, timolol is a non-selective beta-adrenergic receptor antagonist indicated for treating glaucoma, heart attacks, hypertension, and migraine headaches. The chemical structure for timolol is:

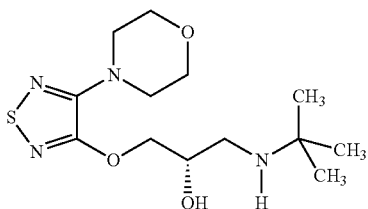 [SMILES: CC(C)(C)NC[C@H](O)COc1nsnc1N1CCOCC1]

In some embodiments, latanoprost is a medication administered into the eyes of a mammal to control the progression of glaucoma or ocular hypertension by reducing intraocular pressure. It is a prostaglandin analog. The chemical structure for latanoprost is:

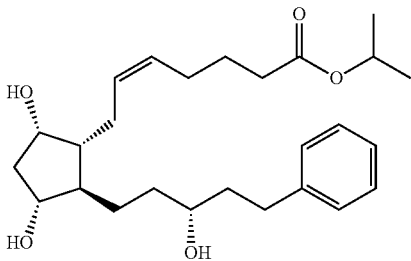 [SMILES: CC(C)OC(=O)CCC/C=C\C[C@@H]1[C@@H](CC[C@@H](O)CCc2ccccc2)[C@H](O)C[C@@H]1O]

In some embodiments of the composition of the present invention, the Carbonic anhydrase inhibitors can be dorzolamide (Trusopt), ation thereofbrinzolamide (Azopt), acetazolamide (Diamox), or any combination thereof Examples of agents used for glaucoma inclu β-blockers (e.g., timolol, betaxolol, levobetaxolol, carteolol, levobunolol, propranolol), carbonic anhydrase inhibitors (e.g., brinzolamide and dorzolamide), al antagonists (e.g., nipradolol), α2 agonists (e.g. iopidine and brimonidine), miotics (e.g., pilocarpine and epinephrine), prostaglandin analogs (e.g., latanoprost, travoprost, unoprostone, and compounds set forth in U.S. Pat. Nos. 5,889,052; 5,296,504; 5,422,368; and 5,151,444), "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and compounds from WO 94/13275, including memantine, where all patents and patent application publications are incorporated herein by reference in their entireties for all purposes. In some embodiments, the composition of the present invention can include Adenosine agonist, Rho Kinase inhibitors and molecules with combined activity such as Latanoparostene Bunod, where a "combined activity" refers to two molecules which are capable of serving two mechanisms of action for reducing intraocular pressure.

In some embodiments of the composition of the present invention, the concentration of the prostaglandin in the composite is 50% to 60% by weight, where the concentration of the prostaglandin in the final plug is between 10% to 20%.

The present invention provides a pharmaceutical composition and glaucoma treatment methods. The present invention is a composition in the form of an implant, where the implant is configured to provide for extended release times of one or more therapeutic agents. In some embodiments, the implant is in the shape of a core. In some embodiments, the implant is in the shape of a plug. In some embodiments, the therapeutic agent is a prostaglandin. In some embodiments, the prostaglandin is latanoprost.

In some embodiments of the composition of the present invention, an implant is configured to release the drug over a period of time, for example, for at least one week or for example for between about two months and about six months, after intraocular administration of a latanoprost containing implant. In some embodiments, the composition further includes timolol. In some embodiments, the period of time is between one month and one year. In some embodiments, the period of time is between one month and nine months. In some embodiments, the period of time is between one month and six months. In some embodiments, the period of time is between one month and three months. In some embodiments, the period of time is between three months and one year. In some embodiments, the period of time is between six months and one year. In some embodiments, the period of time is between nine months and one year. In some embodiments, the period of time is between three months and nine months. In some embodiments, the period of time is between three months and six months. In some embodiments, the period of time is between six months and nine months.

In an embodiment of the composition of the present invention, a composition is a pharmaceutical composition plug configured to provide an intraocular use, e.g., to treat ocular condition. In some embodiments, the pharmaceutical composition is a plug comprising a solid composite powder, where the solid composite powder is dispersed in at least one soft polymer. In some embodiments, the solid composite powder includes an organic particulate including a bio-active agent, inert carrier, binder, or any combination thereof. In some embodiments of the composition of the present invention, an organic particulate is configured to absorb a drug, i.e., is configured carry the drug (i.e., a drug carrier; e.g., but not limited to, fumed silica). The organic particulate can have a surface area between 5 to 1000 m^2/gram (fumed silica surface area is 10-600 m2/gr; silica gel around 800 m2/gr; calcium carbonate surface area is 5-24 m2/gr).

In some embodiments of the composition of the present invention, the bio-active agent can be dissolved, dispersed, emulsified, bound, adsorbed, impregnated, mixed, or otherwise placed into a solid organic matrix. In some embodiments, the bio-active agent may be directly mixed in with the organic matrix. In some embodiments, the bio-active agent may be adsorbed to another material, e.g., a particulate and/or fibrous matter, which can be mixed with the organic matrix.

In some embodiments of the composition of the present invention, the bio-active agent is first dissolved, dispersed, or emulsified into an organic compound (or, e.g., its precursors) melt, solution, emulsion or dispersion. In some embodiments, the solid organic matrix can be comprised of polymers, oligomers, monomers, wax, oils, plasticizers, and any combinations thereof.

In some embodiments of the composition of the present invention, the organic particulate comprising the drug (e.g., a prostaglandin, e.g., latanoprost) can be mixed with at least one inert pharmaceutically acceptable excipient or carrier, such as, but not limited to, sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay and pectin (i) lubricants such as talc, calcium stearate, magnesium stearate, solid polyethylene glycols, sodium lauryl sulfate, or any combination thereof.

In some embodiments of the composition of the present invention, the organic particulate and the inert carrier are bound together with a binder to generate the composite matrix. In some embodiments, exemplary polymers include, but are not limited to, poly(dimethylsiloxane), polyurethanes, epoxies, methyl methacrylate polymers, acrylic copolymers, polyesters, polyamides, polyethylene, polypropylene, ethylene copolymers and terpolymers, propylene copolymers and terpolymers, fluoropolymers, vinyls, styrenics, polycarbonates, amino resins, and phenolic resins. Other exemplary polymers include crosslinked acrylic or methacrylic networks, including networks formed by ultraviolet (UV) curing. In some embodiments, the core (where the drug is absorbed or exist) comprises a thermosetting polymer. In some embodiments, exemplary waxes include, but are not limited to, paraffins, amides, esters, fatty acid derivatives, fatty alcohol derivatives, silicones, and phospholipids.

In some embodiments of the composition of the present invention, the composite matrix containing a bio-active agent (e.g., but not limited to, a prostaglandin, e.g., but not limited to, latanoprost) can be in a solid form such as powder, flakes, fibers, or any combination thereof. In some embodiments, the composite can be milled and/or micronized to the size of a fine powder <100 μm or to size <30 μm, using milling apparatus like mortar and pestle, electronic grinder, etc. In some embodiments, the fine composite powder can be dispersed and/or mixed with a flexible polymer. In some embodiments, the flexible polymer can be a medical polymer such as, e.g., including a polymer having hydrophilic and/or hydrophobic characteristics. In some embodiments, exemplary polymers include, but are not limited to: a silicone, a polyacrylate, a polyurethane, or a combination of two or more of the polymers.

In some embodiments of the composition of the present invention, polyurethanes can be shaped as desired, or its permeability can be tailored as desired, to achieve a predetermined release rate of the bio-active agent from the device to the patient. In some embodiments, the polymer comprises one or more polymers, made of the homopolymers or heteropolymers.

In some embodiments of the composition of the present invention, a mixture includes (1) a polymer and (2) a powder, which is formed into a solid, self-supporting shape. In some embodiments, the self-supporting shape can be the desired shape of the composition (i.e., the solid core), further processed by, e.g., trimming or cutting, into the desired shape. In some embodiments, a shape can be, but is not limited to, a cylinder, plug, coin, disk, plate, cube, sphere, fiber, box, diamond, ring, "S", "L", "T", web, net, mesh, "U", or "V".

In some embodiments of the composition of the present invention, an outer shell coating may be added to the exterior of a solid core. In some embodiments, the coating comprises a second non-biodegradable polymer that is substantially impermeable to a therapeutic compound (e.g., but not limited to, a prostaglandin, e.g., latanoprost). In some embodiments, the coating is at least less permeable (e.g., 1% less permeable, 5% less permeable, 10% less permeable, 20% less permeable, 30% less permeable, 40% less permeable, 50% less permeable, 60% less permeable, 70% less permeable, etc.) to the therapeutic compound compared with the permeability of the therapeutic compound to the first non-biodegradable polymer. In some embodiments, the outer shell coating can be butvar and/or parylene.

Figure 1A:
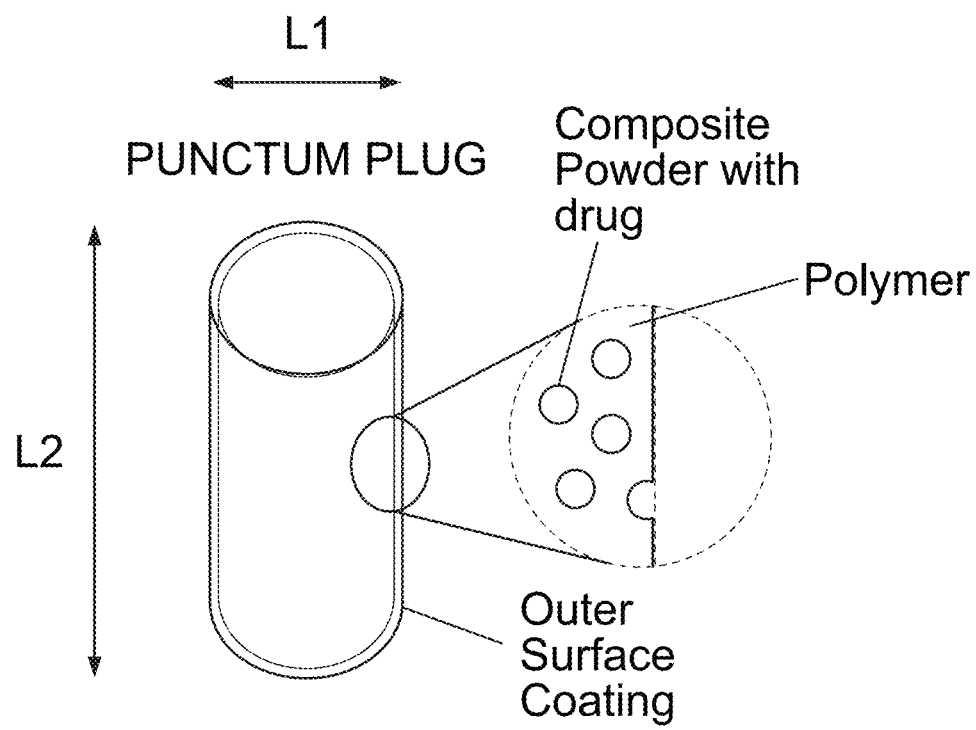
FIGS. 1A-C illustrate embodiments of the composition of the present invention, showing various plugs.
Figure 1B:
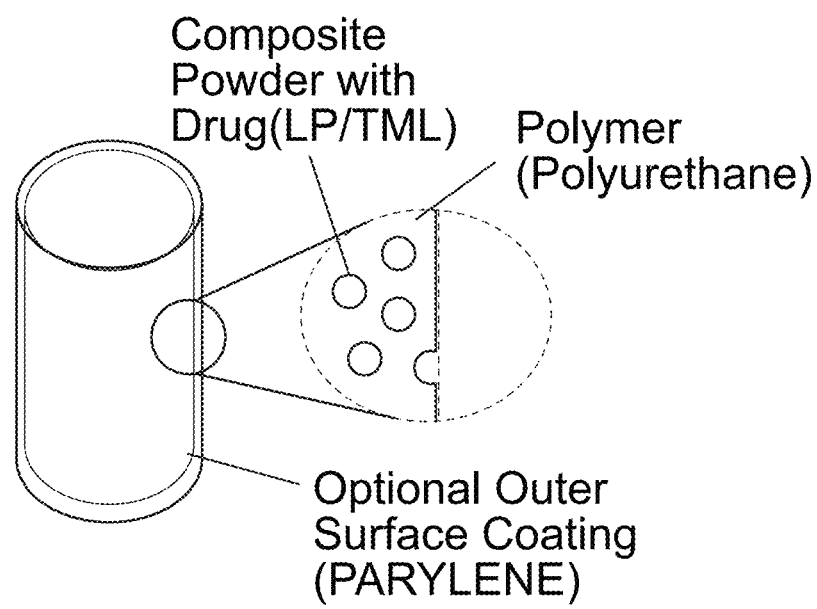
Figure 1C:
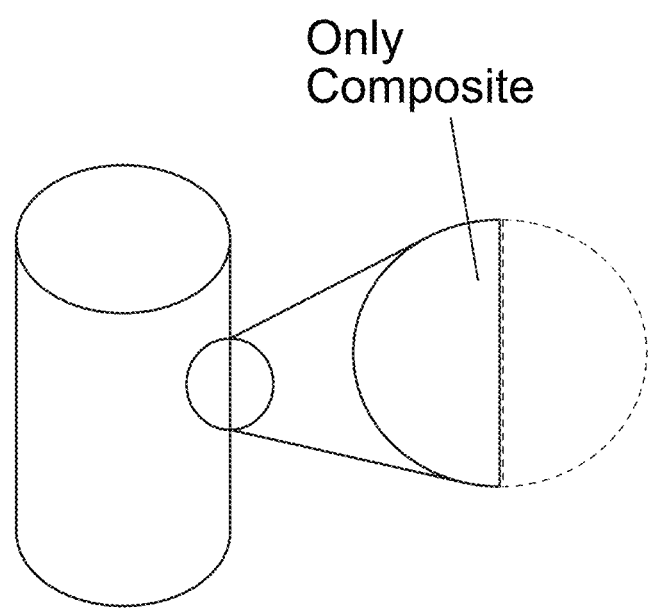

FIG. 1A-C illustrates an embodiment of the present invention, showing a schematic drawing of the device, with composite powder dispersed in polymer.

Figure 2A:
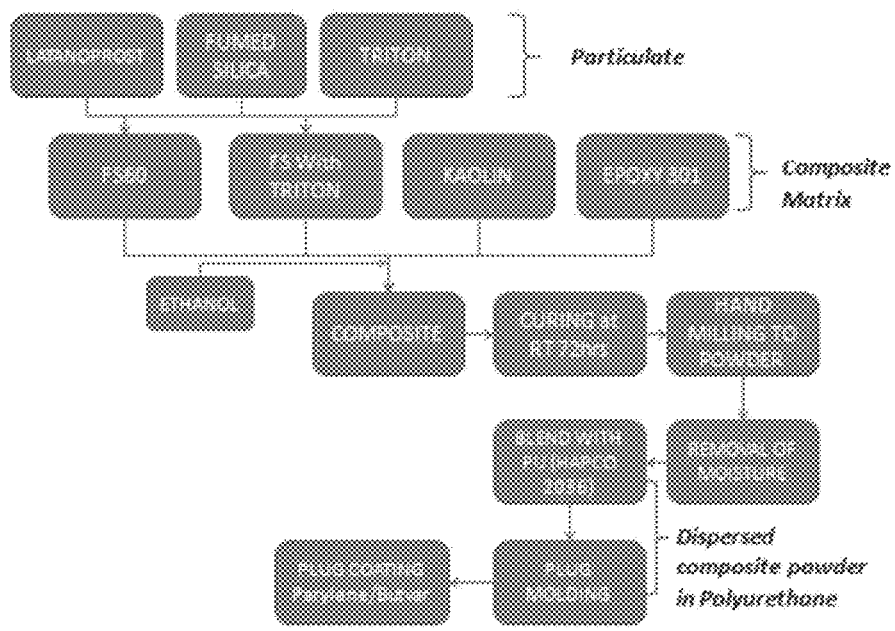
FIGS. 2A and B illustrate embodiments of the process for generating the composition of the present invention.
Figure 2B:
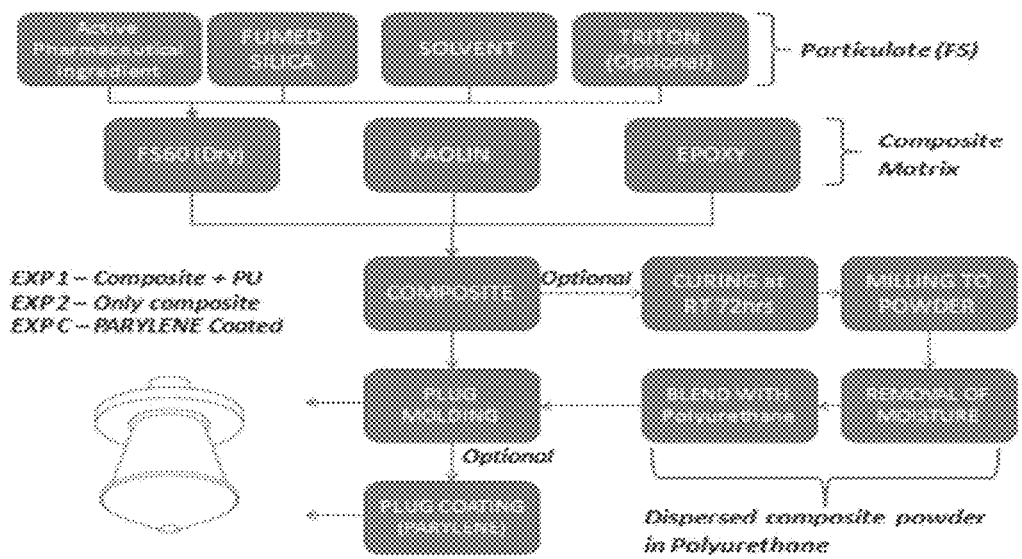

FIGS. 2A and 2B illustrates an embodiment of the present invention, showing a schematic drawing of the process.

Figure 3:
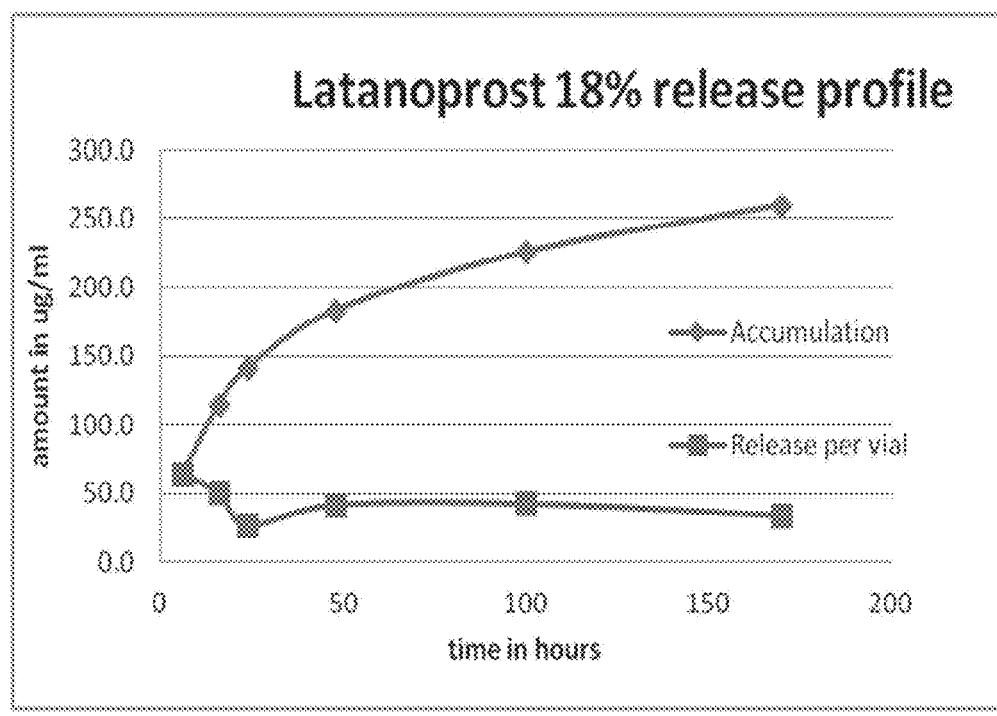
FIG. 3 illustrates an embodiment of the composition of the present invention, showing a release profile.

FIG. 3 illustrates an embodiment of the present invention, showing a graph of in vitro percentage cumulative release of latanoprost from a plug sample over a test period measuring 7 days.

FIGS. 4-7 illustrate embodiments of the placement of the composition of the present invention in a human eye.

FIG. 8 is a schematic depiction of liquid at the surface of a non-porous particle (left) and of liquid absorbed in the pores of fumed silica (right).

The present invention describes a drug delivery device including: 1) particles of inert materials, absorbed with drug on surface of particles or inside porosity; 2) inert polymer matrix, where drug-inert particles are dispersed, where the polymer has no chemical interaction with drug and is providing mechanical package, and where the concentration of drug on particles, and the loading of particles in polymer matrix, is configured to control drug reservoir capacity; 3) an hydrophobic flexible polymer, which connects the polymer matrix into a shape and creates a barrier for drug release; 4) where the hydrophobic polymer is insufficient for controlling the release, a perforated outer barrier is applied to the solid core. In some embodiments, the permeability, and/or size and number of apertures in barrier are configured to control a release rate of the drug (e.g., but not limited to, a prostaglandin, but not limited to, e.g. latanoprost).

In some embodiments, the composition of the present invention includes: (i) a first pharmaceutical agent, a bulking agent, at least one inert material configured to have an increased surface area and a bulk density of between 1-3 gr/cm3 (e.g., but not limited to, 1 gr/cm3, 1.1 gr/cm3, 1.2 gr/cm3, etc.). In some embodiments, the first pharmaceutical agent is a prostaglandin or a prostaglandin analog. In some embodiments, the prostaglandin is selected from a group including: cloprostenol, fluprostenol, latanoprost, travoprost, unoprostone, and any combination thereof. In some embodiments, the composition further includes a second pharmaceutical agent, where the second pharmaceutical agent is an alpha agonist selected from the group including: iopidine and/or brimonidine. In some embodiments, the second pharmaceutical agent is a beta-blocker, where the beta-blocker is selected from the group including: timolol, betaxolol, levobetaxolol, carteolol, levobunolol, propranolol, and any combination thereof. In some embodiments, the composition further includes a third pharmaceutical agent, where the third pharmaceutical agent is an alpha agonist selected from the group including: iopidine and/or brimonidine.

In some embodiments, the composition of the present invention includes: cloprostenol, kaolin, and fumed silica. In some embodiments, the composition of the present invention includes: cloprostenol, iopidine, kaolin, and fumed silica. In some embodiments, the composition of the present invention includes: cloprostenol, brimonidine, kaolin, and fumed silica. In some embodiments, the composition of the present invention includes: cloprostenol, timolol, kaolin, and fumed silica. In some embodiments, the composition of the present invention includes: cloprostenol, timolol, iopidine, kaolin, and fumed silica. In some embodiments, the composition of the present invention includes: cloprostenol, timolol, brimonidine, kaolin, and fumed silica.

In some embodiments, the composition of the present invention includes: cloprostenol, betaxolol, kaolin, and fumed silica. In some embodiments, the composition of the present invention includes: cloprostenol, betaxolol, iopidine, kaolin, and fumed silica. In some embodiments, the composition of the present invention includes: cloprostenol, betaxolol, brimonidine, kaolin, and fumed silica.

In some embodiments, the composition of the present invention includes: cloprostenol, levobetaxolol, kaolin, and fumed silica. In some embodiments, the composition of the present invention includes: cloprostenol, levobetaxolol, iopidine, kaolin, and fumed silica. In some embodiments, the composition of the present invention includes: cloprostenol, levobetaxolol, brimonidine, kaolin, and fumed silica.

In some embodiments, the composition of the present invention includes: cloprostenol, carteolol, kaolin, and fumed silica. In some embodiments, the composition of the present invention includes: cloprostenol, carteolol, iopidine, kaolin, and fumed silica. In some embodiments, the composition of the present invention includes: cloprostenol, carteolol, brimonidine, kaolin, and fumed silica.

In some embodiments, the composition of the present invention includes: cloprostenol, levobunolol, kaolin, and fumed silica. In some embodiments, the composition of the present invention includes: cloprostenol, levobunolol, iopidine, kaolin, and fumed silica. In some embodiments, the composition of the present invention includes: cloprostenol, levobunolol, brimonidine, kaolin, and fumed silica.

In some embodiments, the composition of the present invention includes: cloprostenol, propranolol, kaolin, and fumed silica. In some embodiments, the composition of the present invention includes: cloprostenol, propranolol, iopidine, kaolin, and fumed silica. In some embodiments, the composition of the present invention includes: cloprostenol, propranolol, brimonidine, kaolin, and fumed silica.

In some embodiments, the composition of the present invention includes: fluprostenol, kaolin, and fumed silica. In some embodiments, the composition of the present invention includes: fluprostenol, iopidine, kaolin, and fumed silica. In some embodiments, the composition of the present invention includes: fluprostenol, brimonidine, kaolin, and fumed silica. In some embodiments, the composition of the present invention includes: fluprostenol, timolol, kaolin, and fumed silica. In some embodiments, the composition of the present invention includes: fluprostenol, timolol, iopidine, kaolin, and fumed silica. In some embodiments, the composition of the present invention includes: fluprostenol, timolol, brimonidine, kaolin, and fumed silica.

In some embodiments, the composition of the present invention includes: fluprostenol, betaxolol, kaolin, and fumed silica. In some embodiments, the composition of the present invention includes: fluprostenol, betaxolol, iopidine, kaolin, and fumed silica. In some embodiments, the composition of the present invention includes: fluprostenol, betaxolol, brimonidine, kaolin, and fumed silica.

In some embodiments, the composition of the present invention includes: fluprostenol, levobetaxolol, kaolin, and fumed silica. In some embodiments, the composition of the present invention includes: fluprostenol, levobetaxolol, iopidine, kaolin, and fumed silica. In some embodiments, the composition of the present invention includes: fluprostenol, levobetaxolol, brimonidine, kaolin, and fumed silica.

In some embodiments, the composition of the present invention includes: fluprostenol, carteolol, kaolin, and fumed silica. In some embodiments, the composition of the present invention includes: fluprostenol, carteolol, iopidine, kaolin, and fumed silica. In some embodiments, the composition of the present invention includes: fluprostenol, carteolol, brimonidine, kaolin, and fumed silica.

In some embodiments, the composition of the present invention includes: fluprostenol, levobunolol, kaolin, and fumed silica. In some embodiments, the composition of the present invention includes: fluprostenol, levobunolol, iopidine, kaolin, and fumed silica. In some embodiments, the composition of the present invention includes: fluprostenol, levobunolol, brimonidine, kaolin, and fumed silica.

In some embodiments, the composition of the present invention includes: fluprostenol, propranolol, kaolin, and fumed silica. In some embodiments, the composition of the present invention includes: fluprostenol, propranolol, iopidine, kaolin, and fumed silica. In some embodiments, the composition of the present invention includes: fluprostenol, propranolol, brimonidine, kaolin, and fumed silica.

In some embodiments, the composition of the present invention includes: latanoprost, kaolin, and fumed silica. In some embodiments, the composition of the present invention includes: latanoprost, iopidine, kaolin, and fumed silica. In some embodiments, the composition of the present invention includes: latanoprost, brimonidine, kaolin, and fumed silica. In some embodiments, the composition of the present invention includes: latanoprost, timolol, kaolin, and fumed silica. In some embodiments, the composition of the present invention includes: latanoprost, timolol, iopidine, kaolin, and fumed silica. In some embodiments, the composition of the present invention includes: latanoprost, timolol, brimonidine, kaolin, and fumed silica.

In some embodiments, the composition of the present invention includes: latanoprost, betaxolol, kaolin, and fumed silica. In some embodiments, the composition of the present invention includes: latanoprost, betaxolol, iopidine, kaolin, and fumed silica. In some embodiments, the composition of the present invention includes: latanoprost, betaxolol, brimonidine, kaolin, and fumed silica.

In some embodiments, the composition of the present invention includes: latanoprost, levobetaxolol, kaolin, and fumed silica. In some embodiments, the composition of the present invention includes: latanoprost, levobetaxolol, iopidine, kaolin, and fumed silica. In some embodiments, the composition of the present invention includes: latanoprost, levobetaxolol, brimonidine, kaolin, and fumed silica.

In some embodiments, the composition of the present invention includes: latanoprost, carteolol, kaolin, and fumed silica. In some embodiments, the composition of the present invention includes: latanoprost, carteolol, iopidine, kaolin, and fumed silica. In some embodiments, the composition of the present invention includes: latanoprost, carteolol, brimonidine, kaolin, and fumed silica.

In some embodiments, the composition of the present invention includes: latanoprost, levobunolol, kaolin, and fumed silica. In some embodiments, the composition of the present invention includes: latanoprost, levobunolol, iopidine, kaolin, and fumed silica. In some embodiments, the composition of the present invention includes: latanoprost, levobunolol, brimonidine, kaolin, and fumed silica.

In some embodiments, the composition of the present invention includes: latanoprost, propranolol, kaolin, and fumed silica. In some embodiments, the composition of the present invention includes: latanoprost, propranolol, iopidine, kaolin, and fumed silica. In some embodiments, the composition of the present invention includes: latanoprost, propranolol, brimonidine, kaolin, and fumed silica.

In some embodiments, the composition of the present invention includes: travoprost, kaolin, and fumed silica. In some embodiments, the composition of the present invention includes: travoprost, iopidine, kaolin, and fumed silica. In some embodiments, the composition of the present invention includes: travoprost, brimonidine, kaolin, and fumed silica. In some embodiments, the composition of the present invention includes: travoprost, timolol, kaolin, and fumed silica. In some embodiments, the composition of the present invention includes: travoprost, timolol, iopidine, kaolin, and fumed silica. In some embodiments, the composition of the present invention includes: travoprost, timolol, brimonidine, kaolin, and fumed silica.

In some embodiments, the composition of the present invention includes: travoprost, betaxolol, kaolin, and fumed silica. In some embodiments, the composition of the present invention includes: travoprost, betaxolol, iopidine, kaolin, and fumed silica. In some embodiments, the composition of the present invention includes: travoprost, betaxolol, brimonidine, kaolin, and fumed silica.

In some embodiments, the composition of the present invention includes: travoprost, levobetaxolol, kaolin, and fumed silica. In some embodiments, the composition of the present invention includes: travoprost, levobetaxolol, iopidine, kaolin, and fumed silica. In some embodiments, the composition of the present invention includes: travoprost, levobetaxolol, brimonidine, kaolin, and fumed silica.

In some embodiments, the composition of the present invention includes: travoprost, carteolol, kaolin, and fumed silica. In some embodiments, the composition of the present invention includes: travoprost, carteolol, iopidine, kaolin, and fumed silica. In some embodiments, the composition of the present invention includes: travoprost, carteolol, brimonidine, kaolin, and fumed silica.

In some embodiments, the composition of the present invention includes: travoprost, levobunolol, kaolin, and fumed silica. In some embodiments, the composition of the present invention includes: travoprost, levobunolol, iopidine, kaolin, and fumed silica. In some embodiments, the composition of the present invention includes: travoprost, levobunolol, brimonidine, kaolin, and fumed silica.

In some embodiments, the composition of the present invention includes: travoprost, propranolol, kaolin, and fumed silica. In some embodiments, the composition of the present invention includes: travoprost, propranolol, iopidine, kaolin, and fumed silica. In some embodiments, the composition of the present invention includes: travoprost, propranolol, brimonidine, kaolin, and fumed silica.

In some embodiments, the composition of the present invention includes: unoprostone, kaolin, and fumed silica. In some embodiments, the composition of the present invention includes: unoprostone, iopidine, kaolin, and fumed silica. In some embodiments, the composition of the present invention includes: unoprostone, brimonidine, kaolin, and fumed silica. In some embodiments, the composition of the present invention includes: unoprostone, timolol, kaolin, and fumed silica. In some embodiments, the composition of the present invention includes: unoprostone, timolol, iopidine, kaolin, and fumed silica. In some embodiments, the composition of the present invention includes: unoprostone, timolol, brimonidine, kaolin, and fumed silica.

In some embodiments, the composition of the present invention includes: unoprostone, betaxolol, kaolin, and fumed silica. In some embodiments, the composition of the present invention includes: unoprostone, betaxolol, iopidine, kaolin, and fumed silica. In some embodiments, the composition of the present invention includes: unoprostone, betaxolol, brimonidine, kaolin, and fumed silica.

In some embodiments, the composition of the present invention includes: unoprostone, levobetaxolol, kaolin, and fumed silica. In some embodiments, the composition of the present invention includes: unoprostone, levobetaxolol, iopidine, kaolin, and fumed silica. In some embodiments, the composition of the present invention includes: unoprostone, levobetaxolol, brimonidine, kaolin, and fumed silica.

In some embodiments, the composition of the present invention includes: unoprostone, carteolol, kaolin, and fumed silica. In some embodiments, the composition of the present invention includes: unoprostone, carteolol, iopidine, kaolin, and fumed silica. In some embodiments, the composition of the present invention includes: unoprostone, carteolol, brimonidine, kaolin, and fumed silica.

In some embodiments, the composition of the present invention includes: unoprostone, levobunolol, kaolin, and fumed silica. In some embodiments, the composition of the present invention includes: unoprostone, levobunolol, iopidine, kaolin, and fumed silica. In some embodiments, the composition of the present invention includes: unoprostone, levobunolol, brimonidine, kaolin, and fumed silica.

In some embodiments, the composition of the present invention includes: unoprostone, propranolol, kaolin, and fumed silica. In some embodiments, the composition of the present invention includes: unoprostone, propranolol, iopidine, kaolin, and fumed silica. In some embodiments, the composition of the present invention includes: unoprostone, propranolol, brimonidine, kaolin, and fumed silica.

In some embodiments, where the composition of the present invention includes at least one active agent (e.g., but not limited to, Latanoprost, unoprostone, propranolol, timolol, etc.), the same amounts of bulking agents and inert materials (e.g., but not limited to, fumed silica, epoxy, and kaolin) will be used to generate the composition as shown in the examples below.

Example: Preparation of Plug/Solid Core

In an example of an embodiment of the composition of the present invention, plug samples containing Latanoprost were prepared. Samples were incubated at 37 degrees Celsius for varying times to determine time effect on Latanoprost release profile from the sample into a polar solution (PBS).

Particulate Preparation

Initially, a bio-active agent was adsorbed or loaded on fumed silica (FS). The bio-active agent was Latanoprost (LP). 0.16 g of FS was mixed with 0.25 g LP dissolved in 2 g solvents 1 THF: 1 Ethanol (w/w). Additional examples of polar solvents are: Methanol, Isopropanol, Acetone, and/or Ethyl acetate. The LP/FS mixture was dried at ambient temperature for 24 hours.

Composite Matrix Preparation 0.13 g of kaolin powder and 0.4 g of FS particulate and 0.13 g medical grade epoxy (EPO-TEK 301, manufactured by Epo-Tek from USA) were mixed together. The mixture was mixed until a paste was formed, where the paste had a viscosity of about 250,000 CP. The paste was cured at ambient temperature for 24 hours. The resulting composition had the characteristics of a solid composite.

Composite Milling and Molding

The solid composite was milled using pestle and mortar. The composite fine powder was mixed with polyurethane in a ratio of 40%:60%. The mixture molded in a polyacetal (DELRIN) mold for 12 hours at ambient room temperature and removed from the mold. This formed the plug shape.

Solution Preparation—Releasing Medium Buffer

The solution included the following: 0.01M PBS, 0.005% BAK, and 0.1% TRITON X-100.

Plug Coating Process

The outer layer coating of the plug can be: (1) Butvar 5% (W/N) in Tetrahydrofuran (THF) as solvent or (2) Parylene coating—Polyurethane plugs were coated with 2-5 μm of parylene using a vapor deposition process. To coat the plug, the plugs were placed in a vacuum deposition chamber (Simtal Coating Ltd.) and a vacuum was drawn in the chamber to approximately 0.1 torr. A parylene dimer (di-para-xylylene) was vaporized at approximately 150° C. Then pyrolysis of the monomer (para-xylylene) was affected at approximately 680° C. and 0.5 torr (e.g., but not limited to, the Aryl-chlorine bond in dichloro[2.2]paracyclophane breaks at 680° C. (standard pyrolysis temperature). The monomer then entered the deposition chamber at approximately room temperature (approximately 25° C.) and was adsorbed and polymerized onto the polyurethane plug.

Final Plug Sample Properties

Composites weight 14.1 grams with 18% Latanoprost. See Table 1 for details:

TABLE 1

| | Plug Sample Name | Hours at 37 In PBS + BAK + Triton | Composite Weight mg | PBS + BAK(0.005%) + TRITON(0.1%) g | PPM | Accumulative PPM |
|---|---|---|---|---|---|---|
| 1 | LP18S-1014-6HR  | 6   | 14.1 | 0.527 | 63.8 | 63.8  |
| 2 | LP18S-1014-12HR | 12  | 14.1 | 0.504 | 51.1 | 114.9 |
| 3 | LP18S-1014-24HR | 24  | 14.1 | 0.553 | 26.8 | 141.7 |
| 4 | LP18S-1014-48HR | 48  | 14.1 | 0.560 | 41.6 | 183.3 |
| 5 | LP18S-1014-96HR | 96  | 14.1 | 0.503 | 42.5 | 225.8 |
| 6 | LP18S-1014-7D   | 168 | 14.1 | 0.548 | 33.9 | 259.7 |

The shell can be parylene or butvar. The organic matrix can be kaolin and/or epoxy. The drug absorbing material is fumed silica. No encapsulation of drug.

In an embodiment, active agent is latanoprost, organic matrix is kaolin, the absorbance material is fumed silica. The solvents for the drug are ethanol and HFE. Drying is performed for 24 hours at RT. The Binder (i.e., for mixing with the drug powder) is epoxy. Molding to plug is RT molding. Additional components may include 0.1% Triton and 0.005% BAK.

Example: Method of Using HPLC-UV to Quantify Latanoprost API from a Solution in the Presence of Benzalkonium Chloride (BAK) and Triton X-100

51 samples of Latanoprost in PBS buffer with BAK and Triton X-100 were analyzed according to the following conditions:

Column: Synergy, MAX-RP 250 mm 4.6 mm, 4 micrometer
Flow rate: 1 mL/min
Detector: UV at 210 nm
Inj. Volume: 5 microliters
Sample Temperature: 10±5° C.
Column Temperature: 25±5° C.
Mobile phase A: 0.05M phosphate buffer pH=3: Acetonitrile ("ACN") (40:60, v/v)
Mobile phase B: ACN
Gradient Program:

| Time (mm) | Mobile Phase (A) | Mobile Phase (B) |
|---|---|---|
| 0    | 100 | 0  |
| 1.0  | 100 | 0  |
| 15.0 | 50  | 50 |
| 15.1 | 100 | 0  |
| 20.0 | 100 | 0  |

Run Time: 20 min
Results:

| Sample ID | NEXTAR RUN # 6 + 9 + 10 | Days at 37° C. in PBS + BAK + Triton | Composite Weight 5 mg | PBS + BAK (0.05%) + TRITON(0.1%) 0.5 g | Amount of Latanoprost (µg/mL) | Amount of Latanoprost (µg) |
|---|---|---|---|---|---|---|
|       | 6-47            | 168 | 4.00 | 0.5920 | 70.7  | 41.9 |
|       | 6-48            | 168 | 5.10 | 0.5040 | 96.8  | 48.8 |
|       | 6-49            | 168 | 4.80 | 0.5160 | 114.3 | 59.0 |
| 10-1  | LP14-0315-1W-C01  | 1  | 5.71 | 0.5331 | 28.0 | 14.9 |
| 10-2  | LP14-0315-3W-C01  | 3  | 5.71 | 0.5339 | 52.3 | 27.9 |
| 10-3  | LP14-0315-5W-C01  | 5  | 5.71 | 0.5318 | 50.3 | 26.7 |
| 10-4  | LP14-0315-7W-C01  | 7  | 5.71 | 0.5336 | 43.9 | 23.4 |
| 10-5  | LP14-0315-9W-C01  | 9  | 5.71 | 0.5343 | 35.4 | 18.9 |
| 10-6  | LP14-0315-14W-C01 | 14 | 5.71 | 0.5345 | 46.1 | 24.6 |
| 10-7  | LP14-0315-21W-C01 | 21 | 5.71 | 0.5331 | 60.3 | 32.2 |
| 10-8  | LP14-0315-28W-C01 | 28 | 5.71 | 0.5315 | 50.2 | 26.7 |
| 10-12 | LP14-0315-1W-C02  | 1  | 5.81 | 0.5320 | 45.6 | 24.3 |
| 10-13 | LP14-0315-3W-C02  | 3  | 5.81 | 0.5319 | 47.4 | 25.2 |
| 10-14 | LP14-0315-5W-C02  | 5  | 5.81 | 0.5293 | 44.8 | 23.7 |
| 10-15 | LP14-0315-7W-C02  | 7  | 5.81 | 0.5187 | 43.0 | 22.3 |
| 10-16 | LP14-0315-9W-C02  | 9  | 5.81 | 0.5191 | 42.2 | 21.9 |
| 10-17 | LP14-0315-14W-C02 | 14 | 5.81 | 0.5264 | 51.7 | 27.2 |
| 10-18 | LP14-0315-21W-C02 | 21 | 5.81 | 0.5140 | 62.3 | 32.0 |
| 10-19 | LP14-0315-28W-C02 | 28 | 5.81 | 0.5099 | 62.7 | 32.0 |
| 10-23 | LP14-0315-1W-P1   | 1  | 4.80 | 0.5080 | 17.9 | 9.1  |
| 10-24 | LP14-0315-3W-P1   | 3  | 4.80 | 0.5158 | 37.5 | 19.4 |
| 10-25 | LP14-0315-5W-P1   | 5  | 4.80 | 0.5138 | 35.7 | 18.4 |
| 10-26 | LP14-0315-7W-P1   | 7  | 4.80 | 0.5132 | 42.9 | 22.0 |
| 10-27 | LP14-0315-9W-P1   | 9  | 4.80 | 0.5146 | 36.9 | 19.0 |
| 10-28 | LP14-0315-14W-P1  | 14 | 4.80 | 0.5007 | 53.7 | 26.9 |
| 10-29 | LP14-0315-21W-P1  | 21 | 4.80 | 0.5203 | 65.8 | 34.2 |
| 10-30 | LP14-0315-28W-P1  | 28 | 4.80 | 0.5122 | 60.3 | 30.9 |
| 10-34 | LP14-0315-1W-P2   | 1  | 5.15 | 0.5232 | 22.7 | 11.9 |
| 10-35 | LP14-0315-3W-P2   | 3  | 5.15 | 0.5211 | 33.1 | 17.2 |

-continued

| Sample ID | NEXTAR RUN # 6 + 9 + 10 | Days at 37° C. in PBS + BAK + Triton | Composite Weight 5 mg | PBS + BAK (0.05%) + TRITON(0.1%) 0.5 g | Amount of Latanoprost (μg/mL) | Amount of Latanoprost (μg) |
|---|---|---|---|---|---|---|
| 10-36 | LP14-0315-5W-P2 | 5 | 5.15 | 0.5195 | 29.9 | 15.5 |
| 10-37 | LP14-0315-7W-P2 | 7 | 5.15 | 0.5261 | 34.4 | 18.1 |
| 10-38 | LP14-0315-9W-P2 | 9 | 5.15 | 0.5206 | 47.0 | 24.4 |
| 10-39 | LP14-0315-14W-P2 | 14 | 5.15 | 0.5151 | 58.6 | 30.2 |
| 10-40 | LP14-0315-21W-P2 | 21 | 5.15 | 0.5204 | 74.5 | 38.8 |
| 10-41 | LP14-0315-28W-P2 | 28 | 5.15 | 0.5192 | 51.4 | 26.7 |
| 9-1 | LP14-0315-1W-PY1 | 1 | 4.46 | 0.5303 | 3.8 | 2.0 |
| 9-2 | LP14-0315-3W-PY1 | 3 | 4.46 | 0.5320 | 6.7 | 3.6 |
| 9-3 | LP14-0315-5W-PY1 | 5 | 4.46 | 0.5309 | 6.1 | 3.2 |
| 9-4 | LP14-0315-7W-PY1 | 7 | 4.46 | 0.5306 | 6.2 | 3.3 |
| 9-5 | LP14-0315-9W-PY1 | 9 | 4.46 | 0.5317 | 6.3 | 3.4 |
| 9-6 | LP14-0315-14W-PY1 | 14 | 4.46 | 0.5381 | 12.2 | 6.6 |
| 9-7 | LP14-0315-21W-PY1 | 21 | 4.46 | 0.5342 | 12.1 | 6.4 |
| 9-8 | LP14-0315-28W-PY1 | 28 | 4.46 | 0.5366 | 12.2 | 6.5 |
| 9-12 | LP14-0315-1W-PY2 | 1 | 4.23 | 0.5367 | 4.7 | 2.5 |
| 9-13 | LP14-0315-3W-PY2 | 3 | 4.23 | 0.5352 | 8.5 | 4.5 |
| 9-14 | LP14-0315-5W-PY2 | 5 | 4.23 | 0.5303 | 7.1 | 3.8 |
| 9-15 | LP14-0315-7W-PY2 | 7 | 4.23 | 0.5320 | 6.6 | 3.5 |
| 9-16 | LP14-0315-9W-PY2 | 9 | 4.23 | 0.5325 | 4.7 | 2.5 |
| 9-17 | LP14-0315-14W-PY2 | 14 | 4.23 | 0.5337 | 7.8 | 4.2 |
| 9-18 | LP14-0315-21W-PY2 | 21 | 4.23 | 0.5322 | 9.6 | 5.1 |
| 9-19 | LP14-0315-28W-PY2 | 28 | 4.23 | 0.5305 | 9.5 | 5.0 |

The composite weight was not taken into account in the above table.

Calculations: the samples were injected as is and quantified against Latanoprost RM from Neore Pharma Group Col. Ltd., using 6 points calibration curve from concentrations of 0.5-50 micrograms/mL.

Example: Chromatographic Method Using HPLC-UV to Quantify Latanoprost API from a Solution in the Presence of BAK and Triton X-100

Thirty two samples of Latanoprost in PBS buffer with BAK and Triton X-100 were analyzed using the following conditions:
Column: Synergy, MAX-RP 250 4.6 mm, 4 micrometer
Flow rate: 1 mL/min
Detector: uV at 210 nm
Inj. Volume: 5 microliters
Sample Temperature: 10±5° C.
Column Temperature: 25±5° C.
Mobile phase A: 0.05M phosphate buffer pH=3 (40:60, v/v)
Mobile phase B: ACN
Gradient Program:

| Time (mm) | Mobile Phase (A) | Mobile Phase (B) |
|---|---|---|
| 0 | 100 | 0 |
| 1.0 | 100 | 0 |
| 15.0 | 50 | 50 |
| 15.1 | 100 | 0 |
| 20.0 | 100 | 0 |

Run Time: 20 min
Results:

| | COMPOSITE FS60 + PU NEXTAR RUN 7 | Days at 37° C. in PBS + BAK + Triton | Composite Weight 3 mg | PBS + BAK(0.005%) + TRITON(0.1%) 0.5 g | Amount of Latanoprost (μg/ml) | Amount of Latanoprost (μg) |
|---|---|---|---|---|---|---|
| 1 | Con2 (PBS + BAK + TRITON + LP) | 28 days at 4° C. | 3.70 | 0.516 | 388.5 | 300.5 |
| 2 | Con3 (PBS + BAK + TRITON + LP) | 28 days at 37° C. | 3.5 | 0.634 | 1521.0 | 964.3 |
| 3 | LP14-1114-1D-E 1 | 1 | 2.0 | 0.548 | 46.6 | 26.6 |
| 4 | LP14-1114-3D-E | 3 | 2.0 | 0.566 | 26.8 | 16.3 |
| 5 | LP14-1114-5D-E | 5 | 2.0 | 0.583 | 25.5 | 14.9 |
| 6 | LP14-1114-7D-E | 7 | 2.0 | 0.571 | 23.7 | 13.5 |
| 7 | LP14-1114-9D-E | 9 | 2.0 | 0.553 | 24.5 | 13.5 |
| 8 | LP14-1114-14D-E | 14 | 2.0 | 0.546 | 37.2 | 20.3 |
| 9 | LP14-1114-1D-F | 1 | 3.6 | 0.526 | 0.57 | 0.30 |
| 10 | LP14-1114-3D.F | 3 | 3.6 | 0.542 | 1.02 | 0.55 |
| 11 | LP14-1114-5D.F | 5 | 3.6 | 0.599 | 0.81 | 0.49 |
| 12 | LP14-1114-7D.F | 7 | 3.6 | 0.549 | 1.31 | 0.72 |
| 13 | LP14-1114-9D.F | 9 | 3.6 | 0.494 | 1.41 | 0.70 |
| 14 | LP14-1114-14D.F | 14 | 3.6 | 0.507 | 3.26 | 1.65 |
| 15 | LP14-1114-1D-G | 1 | 2.8 | 0.544 | 6.0 | 3.3 |
| 16 | LP14-1114-3D-G | 3 | 2.8 | 0.515 | 3.7 | 1.9 |

-continued

| | COMPOSITE FS60 + PU NEXTAR RUN 7 | Days at 37° C. in PBS + BAK + Triton | Composite Weight 3 mg | PBS + BAK(0.005%) + TRITON(0.1%) 0.5 g | Amount of Latanoprost (μg/ml) | Amount of Latanoprost (μg) |
|---|---|---|---|---|---|---|
| 17 | LP14-1114-5D-G | 5 | 2.8 | 0.575 | 3.7 | 2.1 |
| 18 | LP14-1114-7D-G | 7 | 2.8 | 0.523 | 6.2 | 3.2 |
| 19 | LP14-1114-9D-G | 9 | 2.8 | 0.618 | 3.7 | 2.3 |
| 20 | LP14-1114-14D-G | 14 | 2.8 | 0.564 | 8.0 | 4.5 |
| 21 | LP14-1114-1D-H | 1 | 3.3 | 0.587 | 24.0 | 14.1 |
| 22 | LP14-1114-3D-H | 3 | 3.3 | 0.611 | 26.4 | 16.1 |
| 23 | LP14-1114-5D-H | 5 | 3.3 | 0.546 | 30.8 | 16.8 |
| 24 | LP14-1114-7D-H | 7 | 3.3 | 0.531 | 32.7 | 17.4 |
| 25 | LP14-1114-9D-H | 9 | 3.3 | 0.504 | 32.9 | 16.6 |
| 26 | LP14-1114-14D-H | 14 | 3.3 | 0.536 | 40.6 | 21.7 |
| 27 | LP14-1114-1D-I | 1 | 2.6 | 0.510 | 10.6 | 5.4 |
| 28 | LP14-1114-3D-I | 3 | 2.6 | 0.580 | 15.7 | 9.1 |
| 29 | LP14-1114-5D-I | 5 | 2.6 | 0.541 | 14.7 | 8.0 |
| 30 | LP14-1114-7D-I | 7 | 2.6 | 0.553 | 21.0 | 11.6 |
| 31 | LP14-1114-9D-I | 9 | 2.6 | 0.539 | 16.1 | 8.7 |
| 32 | LP14-1114-14D-I | 14 | 2.6 | 0.549 | 27.3 | 15.0 |

Calculations: the samples were injected and quantified against Latanoprost RM using 6 points weighted calibration curve from 0.5-50 micrograms/mL concentrations.

Example: Chromatographic Method by HPLC-UV which Will be Suitable to Quantify Latanoprost API from Solution in Presence of BAK and Triton X-100

Thirty four samples of latanoprost in PBS buffer with BAK and Triton X-100 were tested using the following method:
Column: Synergy, MAX-RP 250 4.6 mm, 4 micrometer
Flow rate: 1 mL/min
Detector: uV at 210 nm
Inj. Volume: 100 microliters
Sample Temperature: 10±5° C.
Column Temperature: 25±5° C.
Mobile phase A: 0.05M phosphate buffer pH=3 (40:60, v/v)
Mobile phase B: ACN
Gradient Program:

| Time (mm) | Mobile Phase (A) | Mobile Phase (B) |
|---|---|---|
| 0 | 100 | 0 |
| 1.0 | 100 | 0 |
| 15.0 | 50 | 50 |
| 15.1 | 100 | 0 |
| 20.0 | 100 | 0 |

Run Time: 20 min
Results (using 5 microliters injection volume):

| Sample No. | COMPOSITE FS60 + PU NEXTAR RUN 6 | Days at 37° C. in PBS + BAK + Triton | Composite Weight (mg) | PBS + BAK(0.005%) + TRITON(0.1%) (g) | Amount of Latanoprost (μg/mL) | Amount of Latanoprost (μg) |
|---|---|---|---|---|---|---|
| 1 | Con2 (PBS + BAK + TRITON + LP) | 28 days at 4° C. | 5.60 | 0.5073 | 216 | 109.6 |
| 2 | Con3 (PBS + BAK + TRITON + LP) | 28 days at 37° C. | 4.4 | 0.5090 | 229 | 116.6 |
| 3 | LP14-1114-3D-A | 3 | 4.0 | 0.5033 | 31.8 | 16.0 |
| 4 | LP14-1114-5D-A | 5 | 4.0 | 0.5270 | 25.5 | 13.4 |
| 5 | LP14-1114-7D-A | 7 | 4.0 | 0.5188 | 27.1 | 14.1 |
| 6 | LP14-1114-9D-A | 9 | 4.0 | 0.5207 | 38.6 | 20.1 |
| 7 | LP14-1114-14D-A | 14 | 4.0 | 0.5189 | 54.3 | 28.2 |
| 8 | LP14-1114-21D-A | 21 | 4.0 | 0.5027 | 41.4 | 20.8 |
| 9 | LP14-1114-25D-A | 25 | 4.0 | 0.5076 | 34.0 | 17.3 |
| 10 | LP14-1114-28D-A | 28 | 4.0 | 0.5243 | 36 | 18.9 |
| 11 | LP14B-1114-3D-B | 3 | 5.1 | 0.5010 | 45.0 | 22.5 |
| 12 | LP14B-1114-5D-B | 5 | 5.1 | 0.5143 | 34.0 | 17.5 |
| 13 | LP14B-1114-7D-B | 7 | 5.1 | 0.5215 | 34.8 | 18.1 |
| 14 | LP14B-1114-9D-B | 9 | 5.1 | 0.4927 | 57.2 | 28.2 |
| 15 | LP14B-1114-14D-B | 14 | 5.1 | 0.4963 | 83.3 | 41.3 |
| 16 | LP14B-1114-21D-B | 21 | 5.1 | 0.5095 | 61.6 | 31.4 |
| 17 | LP14B-1114-25D-B | 25 | 5.1 | 0.5277 | 49.1 | 25.9 |
| 18 | LP14B-1114-28D-B | 28 | 5.1 | 0.5065 | 55.5 | 28.1 |
| 19 | LP14-1114-3D-C | 3 | 4.8 | 0.5128 | 41.0 | 21.0 |
| 20 | LP14-1114-5D-C | 5 | 4.8 | 0.5065 | 37.9 | 19.2 |
| 21 | LP14-1114-7D-C | 7 | 4.8 | 0.5202 | 42.9 | 22.3 |
| 22 | LP14-1114-9D-C | 9 | 4.8 | 0.5224 | 70.4 | 36.8 |
| 23 | LP14-1114-14D-C | 14 | 4.8 | 0.5036 | 95.4 | 48.0 |
| 24 | LP14-1114-21D-C | 21 | 4.8 | 0.5267 | 64.8 | 34.1 |
| 25 | LP14-1114-25D-C | 25 | 4.8 | 0.5054 | 63.5 | 32.1 |
| 26 | LP14-1114-28D-C | 28 | 4.8 | 0.5097 | 58.5 | 29.8 |

-continued

| Sample No. | COMPOSITE FS60 + PU NEXTAR RUN 6 | Days at 37° C. in PBS + BAK + Triton | Composite Weight (mg) | PBS + BAK(0.005%) + TRITON(0.1% (g) | Amount of Latanoprost (μg/mL) | Amount of Latanoprost (μg) |
|---|---|---|---|---|---|---|
| 27 | LP14B-1114-3D-D | 3 | 5.0 | 0.5282 | 36.4 | 19.2 |
| 28 | LP14B-1114-5D-D | 5 | 5.0 | 0.5133 | 31.5 | 16.2 |
| 29 | LP14B-1114-7D-D | 7 | 5.0 | 0.5366 | 34.3 | 18.4 |
| 30 | LP14B-1114-9D-D | 9 | 5.0 | 0.5285 | 38.1 | 20.1 |
| 31 | LP14B-1114-14D-D | 14 | 5.0 | 0.5097 | 64.7 | 33.0 |
| 32 | LP14B-1114-21D-D | 21 | 5.0 | 0.5134 | 49.1 | 25.2 |
| 33 | LP14B-1114-25D-D | 25 | 5.0 | 0.5009 | 39.8 | 19.9 |
| 34 | LP14B-1114-28D-D | 28 | 5.0 | 0.5071 | 38.6 | 19.6 |

Notes:
The composite weight does not taken into account.

Calculations samples were injected and quantified against latanoprost RM using 6 points calibration curve from 0.04-50 micrograms/mL concentrations.

Example: HPLC Method for Determining Timolol Maleate™ in Solution Containing Latanoprost, PBS, Benzalkonium Chloride (BAK) and Triton x-100, Using a C-18 Column and a UV Detection at 285 nm For™ and 210 nm for Latanoprost Forty eight samples were analyzed using a Waters Alliance HPLC equipped with UV Detector, a micro analytical balance, Mettler Toledo, MX (QC-601), and a magnetic stirrer.

Linearity of TM was demonstrated in the range from 1-265 micrograms/mL with a square correlation coefficient of 1.0. The limit of quantitation was evaluated on standard solution at concentration of 1 microgram/mL and a signal to noise ratio of 88 was found.

Linearity of Latanoprost was demonstrated in the range from 0.48-240 micrograms/mL with a square correlation coefficient of 0.9999. The limit of quantitation was evaluated on standard solution at concentration of 0.48 micrograms/mL and a signal to noise ratio of 14.8 was found.

Analytical method development and conditions: HPLC method was developed for the determination and quantitation of Timolol Maleate and Latanoprost in aqueous solution containing PBS, BAK and Triton X-100. The chromatographic conditions were as follows:

| Parameter | Analytical condition |
|---|---|
| HPLC Column | Synergi, 4 μ, MAX-RP 80A, 250x4.6mm, 5 μm Cat. No. OOG-4337-EO, Nextar No. 86A-1 |
| Mobile Phase | A: 0.1% TFA in water: Acetonitrile 70:30,(v/v) B: 0.1% TFA in Acetonitrile |
| Gradient Program | see table below |
| Flow Rate | 1.0 mL/min |
| Injection Volume | 20 μL |
| Auto sampler temperature | 10° C. ± 5° C. |
| Column oven temperature | 40° C. ± 5° C. |
| Detection | UV at 210 nm for Latanoprost UV at 285 nm for TM |

Gradient Program:

| Time (mm) | Mobile Phase (A) | Mobile Phase (B) |
|---|---|---|
| 0 | 100 | 0 |
| 3.0 | 100 | 0 |
| 16.0 | 0 | 100 |
| 16.1 | 100 | 0 |
| 22.0 | 100 | 0 |

The sample diluent was 85% water and 15% methanol.

Results: the following parameters were evaluated during the method development: specificity, linearity and range, detection limit and quantitation limit.

Specificity: the sample diluent (85% water:15% methanol) was injected for the specificity test. No interference was detected at the retention time of TM and Latanoprost.

Figure 12:
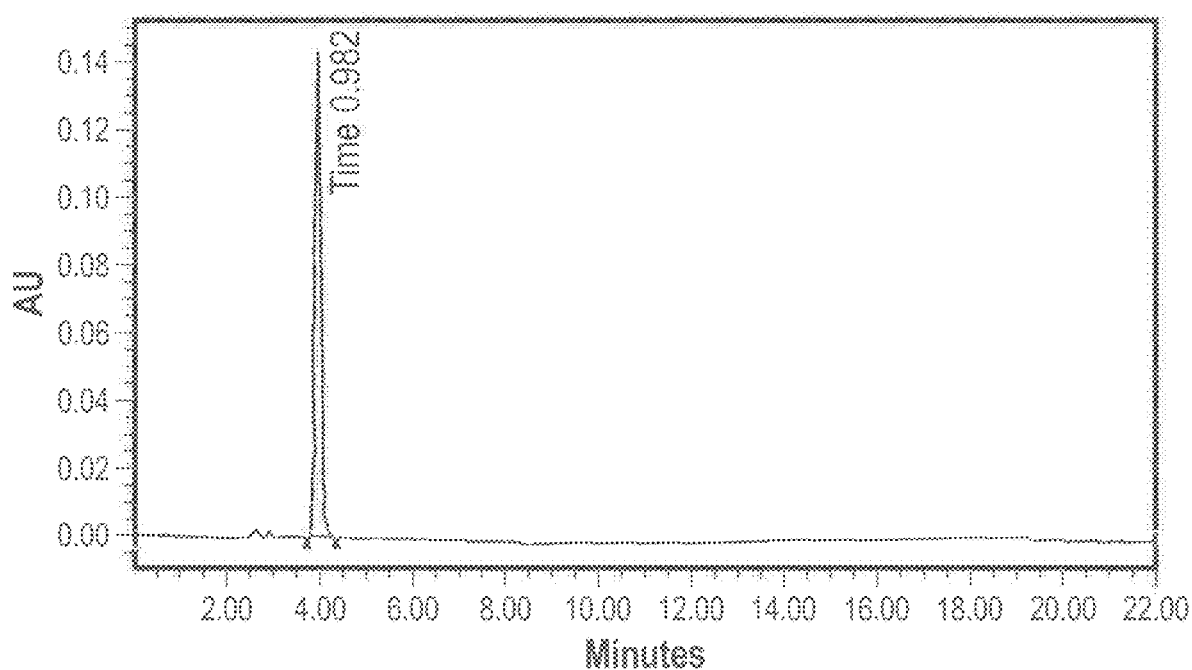
FIG. 12 illustrates a chromatogram of an embodiment of the composition of the present invention.

Linearity Tests:

TM: The linearity of Tm was evaluated from a concentration of 0.53-265 micrograms/mL. Seven standard solutions were prepared separately in order to test the linearity of the HPLC method: 0.53 micrograms/mL, 2.65 micrograms/mL, 13.3 micrograms/mL, 26.5 micrograms/mL, 53.0 micrograms/mL, 132.6 micrograms/mL, and 265.3 micrograms/mL. The correlation between the instrument response and concentration was demonstrated with a squared correlation coefficient of 1.0. FIG. 12 shows the chromatogram results of the TM standard solution at 53 micrograms/mL, where an injection volume of 20 microliters was used for a run time of 22 minutes.

Figure 13:
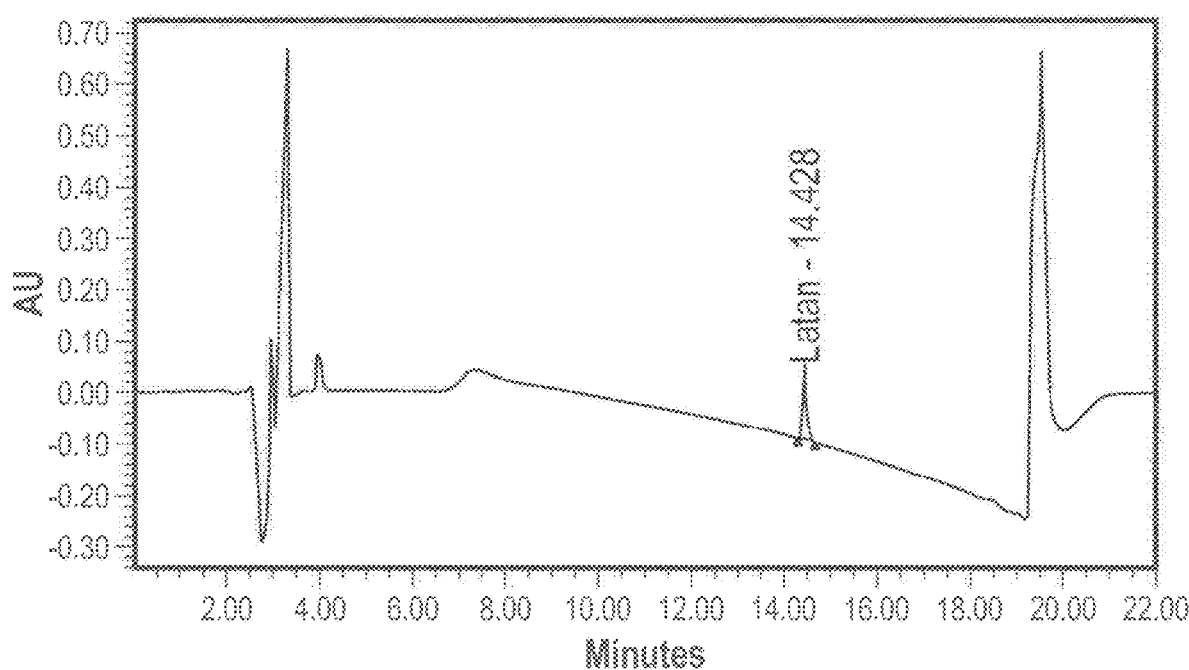
Figure 14A:
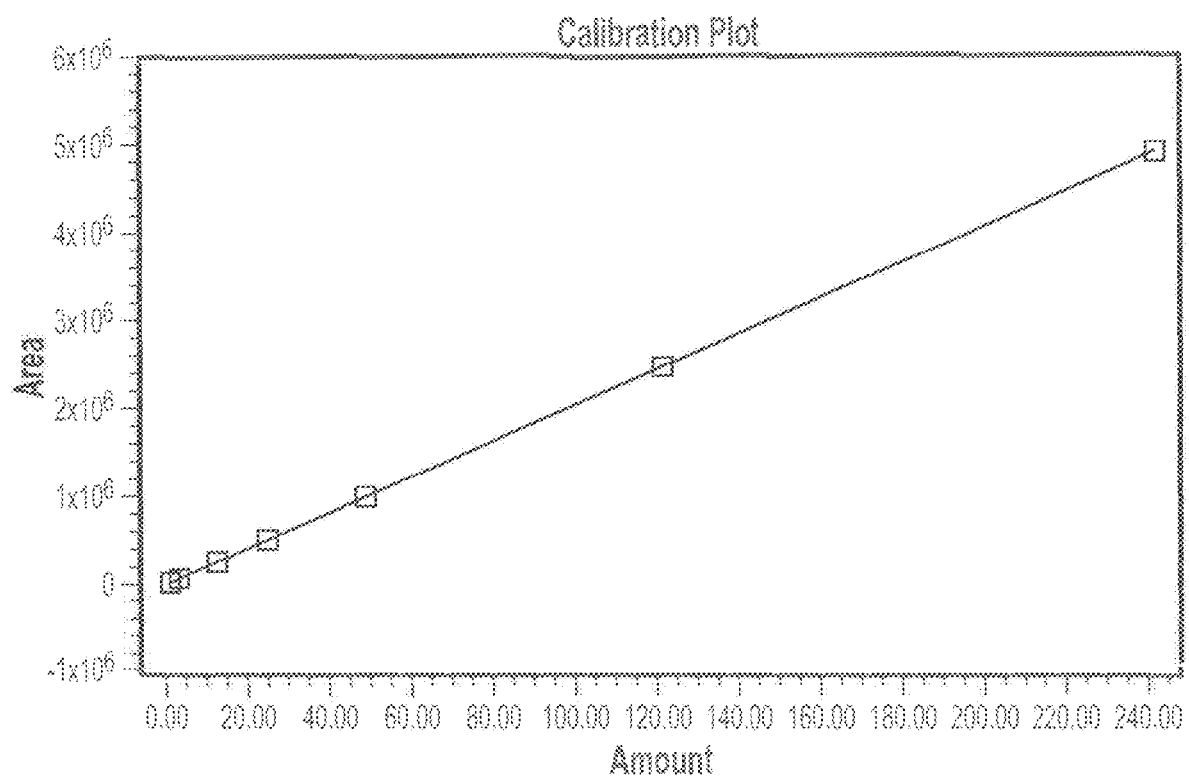

Latanoprost: The linearity of Latanoprost was evaluated from a concentration of 0.48 micrograms/mL to 241 micrograms/mL. Seven standard solutions were prepared separately to test the linearity of the HPLC method: 0.48 micrograms/mL, 2.41 micrograms/mL, 12.0 micrograms/mL, 24.1 micrograms/mL, 48.1 micrograms/mL, 120.3 micrograms/mL, and 240.6 micrograms/mL. A correlation between the instrument response and concentration was demonstrated with a squared correlation coefficient (R2) of 1.0. FIGS. 13 and 14A-B illustrate a typical chromatogram of a standard solution at a concentration of 48 micrograms/mL and calibration curve results, respectively.

Figure 15:
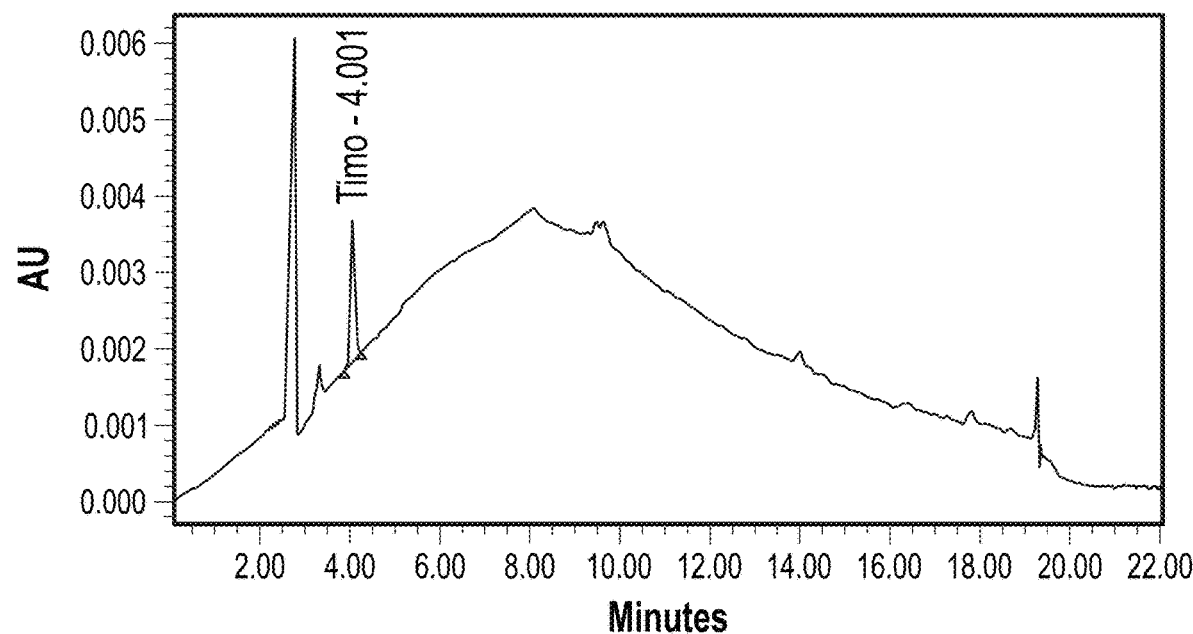
FIG. 15 illustrates a signal to noise ratio of an embodiment of the composition of the present invention.

Limit of Quantitation and Limit of Detection:

Limit of quantitation for TM: the limit of detection (LOD) and the limit of quantitation (LOQ) values were determined by testing standard solution at a concentration of 0.53 micrograms/mL. As used herein, LOD refers to the lowest amount of analyte that can be detected above baseline noise, but not necessarily quantified as an exact value. As used herein, LOQ refers to the lowest amount of analyte which can be reproducibly quantitated above the baseline noise. The signal-to-noise ratio (S/N) for LOD should be about 3 and for LOQ about 10. A signal to noise ratio of 89 was found at standard solution containing 0.53 micrograms/mL. FIG. 15 shows a signal to noise ratio of 88.589 for TM at 285 nm.

Figure 16:
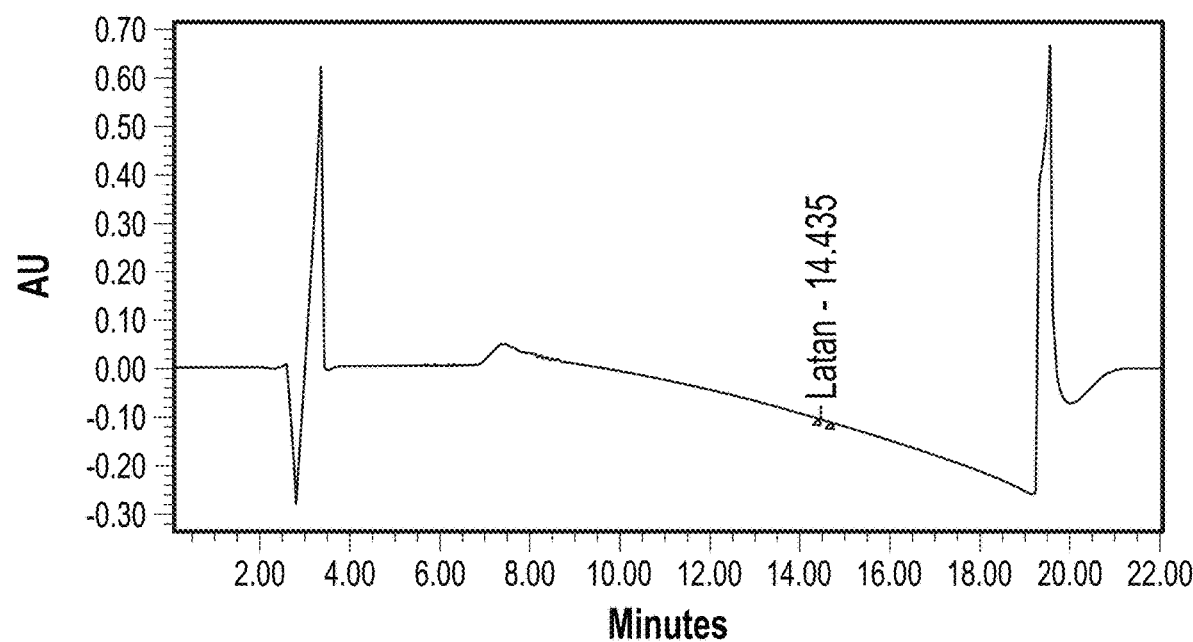
FIG. 16 illustrates a signal to noise ratio of an embodiment of the composition of the present invention.
Figure 17:
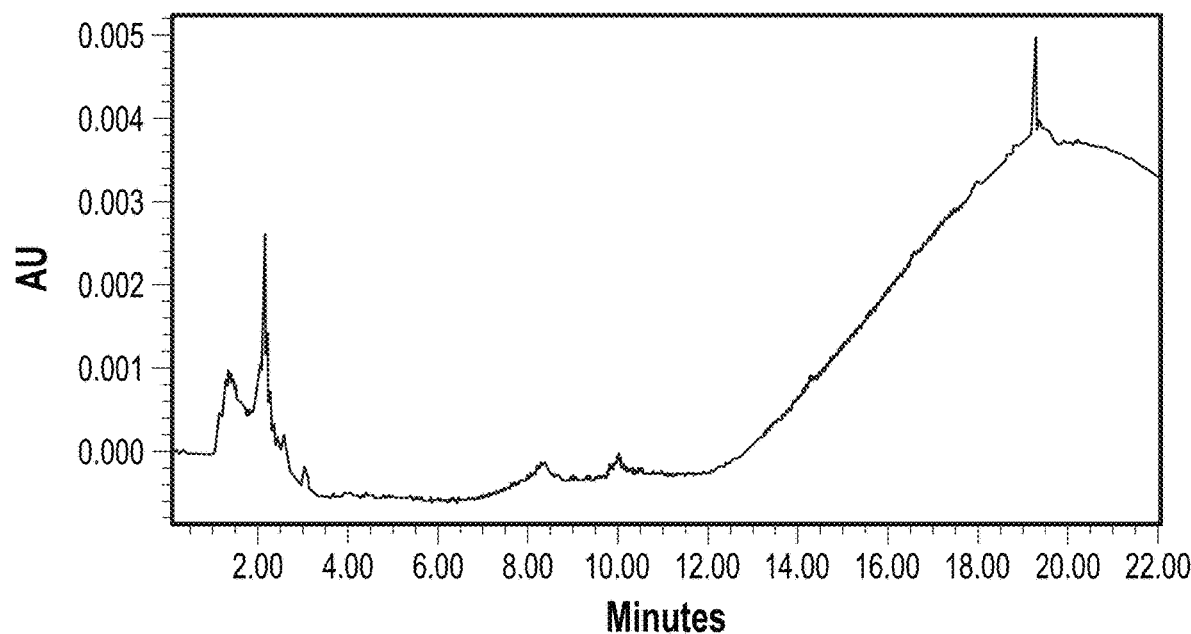
FIGS. 17, 18, 19A-B illustrate chromatograms of embodiments of the compositions of the present invention.
Figure 18:
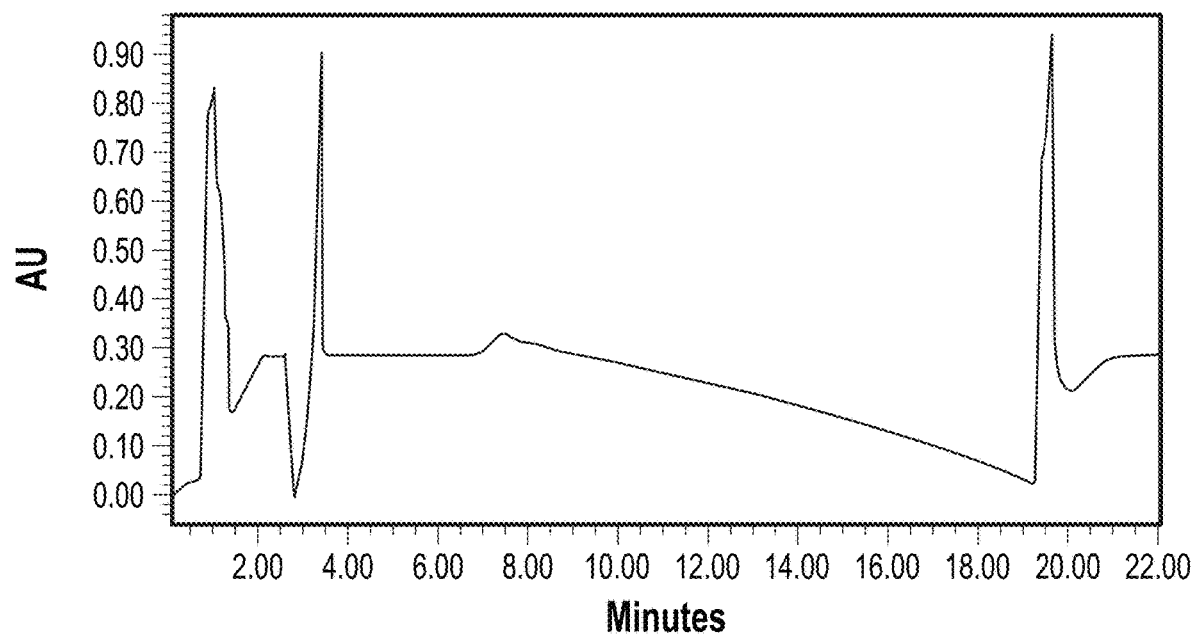

Limit of quantitation for Latanoprost: The LOD and the LOQ values were determined. The signal-to noise ratio (S/N) for LOD is about 3 and for LOQ is about 10. A signal to noise ratio of 14.8 was found at standard solution containing 0.48 micrograms/mL, and is shown in FIG. 16.

System suitability parameters: The system suitability test is performed to demonstrate that the system is fit for the purpose of the analysis, and the following parameters were tested: percent RSD of 5 replicates of the standard solution, tailing factor (T), resolution (R), and number of theoretical plates (N). The table below shows the results of a sample:

| API Name | Tailing Factor (T) | Theoretical Plates (P) | Resolution* (R) |
|---|---|---|---|
| TM | 1.3 | 8469 | 2.0 |
| Latanoprost | 1.3 | 112292 | 1.2 |

*Resolution of API to nearest peak

System precision: the system precision was demonstrated on control standard at a nominal concentration of 50 micrograms/mL. The percent relative standard deviation (RSD) was calculated from the beginning of the sequence log until the end of the sequence log. RSD of less than 2% was found for both API's in all standard injections. The results are shown in the table below:

| | Std | |
|---|---|---|
| Replicate | TM Peak area (AU) | Latanoprost Peak area (AU) |
| Injection 1 | 989723 | 1157736 |
| Injection 2 | 984361 | 1152543 |
| Injection 3 | 990732 | 1143846 |
| Injection 4 | 982226 | 1139423 |
| Injection 5 | 981758 | 1135124 |
| Injection 6 | 975390 | 1129086 |
| Injection 7 | 976605 | 1128033 |
| Injection 8 | 982001 | 1131109 |
| Injection 9 | 977782 | 1130783 |
| Mean | 982286 | 1138631 |
| (%) RSD | 0.5 | 0.9 |

Sample preparation: the sample solutions were shaken using a vortex shaker and transferred into an HPLC vial. The sample solutions were injected into HPLC as is without further dilution. Results are shown in the table below:

| Sample ID | NEXTAR RUN 12 (TIMOLOL) | Days at 37° C. | Composite Weight (mg) | Sample Volume (mL) | Amount of Latanoprost (µg/mL) | Amount of Latanoprost (µg) | Amount of Timolol (µg/mL) | Amount of Timolol (µg) |
|---|---|---|---|---|---|---|---|---|
| 12-1 | LP&TML-0615-1d-C01 | 1 | 5.91 | 0.524 | 17.2 | 9.0 | 1049.1 | 549.7 |
| 12-2 | LP&TML-0615-3d-C01 | 3 | 5.91 | 0.526 | 53.8 | 28.3 | 446.4 | 234.8 |
| 12-3 | LP&TML-0615-5d-C01 | 5 | 5.91 | 0.501 | 74.3 | 37.2 | 162.2 | 81.3 |
| 12-4 | LP&TML-0615-7d-C01 | 7 | 5.91 | 0.514 | 78.1 | 40.1 | 56.3 | 28.9 |
| 12-5 | LP&TML-0615-9d-C01 | 9 | 5.91 | 0.519 | 55.5 | 28.8 | 11.0 | 5.7 |
| 12-6 | LP&TML-0615-14d-C01 | 14 | 5.91 | 0.519 | 104.3 | 54.1 | 5.6 | 2.9 |
| 12-7 | LP&TML-0615-21d-C01 | 21 | 5.91 | 0.518 | 85.2 | 44.1 | 0.9 | 0.5 |
| 12-8 | LP&TML-0615-28d-C01 | 28 | 5.91 | 0.520 | 89.2 | 46.4 | 1.9 | 1.0 |
| 12-12 | LP&TML-0615-1d-C02 | 1 | 6.00 | 0.517 | 17.6 | 9.1 | 944.2 | 488.1 |
| 12-13 | LP&TML-0615-3d-C02 | 3 | 6.00 | 0.517 | 52.8 | 27.3 | 448.2 | 231.7 |
| 12-14 | LP&TML-0615-5d-C02 | 5 | 6.00 | 0.527 | 59.0 | 31.1 | 162.2 | 85.5 |
| 12-15 | LP&TML-0615-7d-C02 | 7 | 6.00 | 0.516 | 82.2 | 42.4 | 77.1 | 39.8 |
| 12-16 | LP&TML-0615-9d-C02 | 9 | 6.00 | 0.520 | 59.2 | 30.8 | 20.5 | 10.7 |
| 12-17 | LP&TML-0615-14d-C02 | 14 | 6.00 | 0.516 | 88.4 | 45.6 | 9.7 | 5.0 |
| 12-18 | LP&TML-0615-21d-C02 | 21 | 6.00 | 0.518 | 102.6 | 53.1 | 1.1 | 0.6 |
| 12-19 | LP&TML-0615-28d-C02 | 28 | 6.00 | 0.518 | 98.0 | 50.8 | 0.3 | 0.2 |
| 12-23 | LP&TML-0615-1d-P1 | 1 | 3.90 | 0.525 | 17.6 | 9.2 | 106.7 | 56.0 |
| 12-24 | LP&TML-0815-3d-P1 | 3 | 3.30 | 0.518 | 30.1 | 15.6 | 100.4 | 52.0 |
| 12-25 | LP&TML-0615-5d-P1 | 5 | 3.90 | 0.520 | 32.5 | 16.9 | 64.8 | 33.7 |
| 12-26 | LP&TML-0615-7d-P1 | 7 | 3.90 | 0.521 | 38.3 | 20.0 | 61.8 | 32.2 |
| 12-27 | LP&TML-0615-9d-P1 | 9 | 3.90 | 0.517 | 26.2 | 13.5 | 31.6 | 16.3 |
| 12-28 | LP&TML-0615-14d-P1 | 14 | 3.90 | 0.514 | 39.5 | 20.3 | 63.5 | 32.6 |
| 12-29 | LP&TML-0615-21d-P1 | 21 | 3.90 | 0.516 | 51.2 | 26.4 | 40.9 | 21.1 |
| 12-30 | LP&TML-0615-28d-P1 | 28 | 3.90 | 0.521 | 39.5 | 20.6 | 13.6 | 7.1 |
| 12-34 | LP&TML-0615-1d-P2 | 1 | 3.50 | 0.524 | 9.1 | 4.8 | 74.4 | 39.0 |
| 12-35 | LP&TML-0615-3d-P2 | 3 | 3.50 | 0.520 | 26.0 | 13.5 | 69.1 | 36.0 |
| 12-36 | LP&TML-0615-5d-P2 | 5 | 3.50 | 0.517 | 28.6 | 14.8 | 48.6 | 25.1 |
| 12-37 | LP&TML-0615-7d-P2 | 7 | 3.50 | 0.522 | 29.2 | 15.2 | 43.6 | 22.8 |
| 12-38 | LP&TML-0615-9d-P2 | 9 | 3.50 | 0.519 | 20.6 | 10.7 | 22.6 | 11.7 |
| 12-39 | LP&TML-0615-14d-P2 | 14 | 3.50 | 0.522 | 35.5 | 18.5 | 51.9 | 27.1 |
| 12-40 | LP&TML-0615-21d-P2 | 21 | 3.50 | 0.516 | 31.0 | 16.0 | 35.0 | 18.1 |
| 12-41 | LP&TML-0615-28d-P2 | 28 | 3.50 | 0.521 | 31.2 | 16.3 | 21.5 | 11.2 |
| 12-48 | LP&TML-0615-1d-TPU | 1 | 7.36 | 0.523 | 14.9 | 7.8 | 1079.0 | 564.3 |
| 12-49 | LP&TML-0615-3d-TPU | 3 | 7.36 | 0.523 | 54.9 | 28.7 | 463.8 | 242.6 |
| 12-50 | LP&TML-0615-5d-TPU | 5 | 7.36 | 0.526 | 64.6 | 34.0 | 140.5 | 73.9 |
| 12-51 | LP&TML-0615-7d-TPU | 7 | 7.36 | 0.512 | 71.8 | 36.8 | 52.0 | 26.6 |
| 12-52 | LP&TML-0615-9d-TPU | 9 | 7.36 | 0.519 | 68.9 | 35.8 | 10.2 | 5.3 |
| 12-53 | LP&TML-0615-14d-TPU | 14 | 7.36 | 0.530 | 90.3 | 47.9 | 4.4 | 2.3 |
| 12-54 | LP&TML-0615-21d-TPU | 21 | 7.36 | 0.528 | 88.9 | 47.0 | 0.9 | 0.5 |
| 12-55 | LP&TML-0615-28d-TPU | 28 | 7.36 | 0.530 | 92.5 | 49.0 | 0.2 | 0.1 |
| 12-60 | LP&TML-0615-1d-TPUSP-_ | 1 | 7.35 | 0.532 | 7.8 | 4.1 | 902.7 | 480.2 |
| 12-61 | LP&TML-0615-7d-TPUSP-_ | 7 | 7.35 | 0.511 | 80.1 | 40.9 | 693.6 | 354.4 |
| 12-62 | LP&TML-0615-1d-TPUSP- | 1 | 5.35 | 0.508 | 21.9 | 11.1 | 834.5 | 423.9 |

-continued

| Sample ID | NEXTAR RUN 12 (TIMOLOL) | Days at 37° C. | Composite Weight (mg) | Sample Volume (mL) | Amount of Latanoprost (µg/mL) | Amount of Latanoprost (µg) | Amount of Timolol (µg/mL) | Amount of Timolol (µg) |
|---|---|---|---|---|---|---|---|---|
| 12-63 | LP&TML-0615-7d-TPUSP-_ | 7 | 5.35 | 0.507 | 97.0 | 49.2 | 896.4 | 454.5 |
| 12-64 | LP&TML-0615-1d-Powder | 1 | 4.11 | 0.504 | 68.5 | 34.5 | 7.3 | 3.7 |
| 12-65 | LP&TML-0615-7d-Powder | 7 | 4.11 | 0.530 | 129.7 | 68.7 | 2.2 | 1.2 |

The composite weight was not taken into the calculations of the above table.

The squared correlation of the linear calibration curve was 1.0 for both API's. The samples were quantified against Latanoprost from Neore Pharmaceutical Group and TM from Signam-Aldrich, Cat. No. T6394.

Figure 19A:
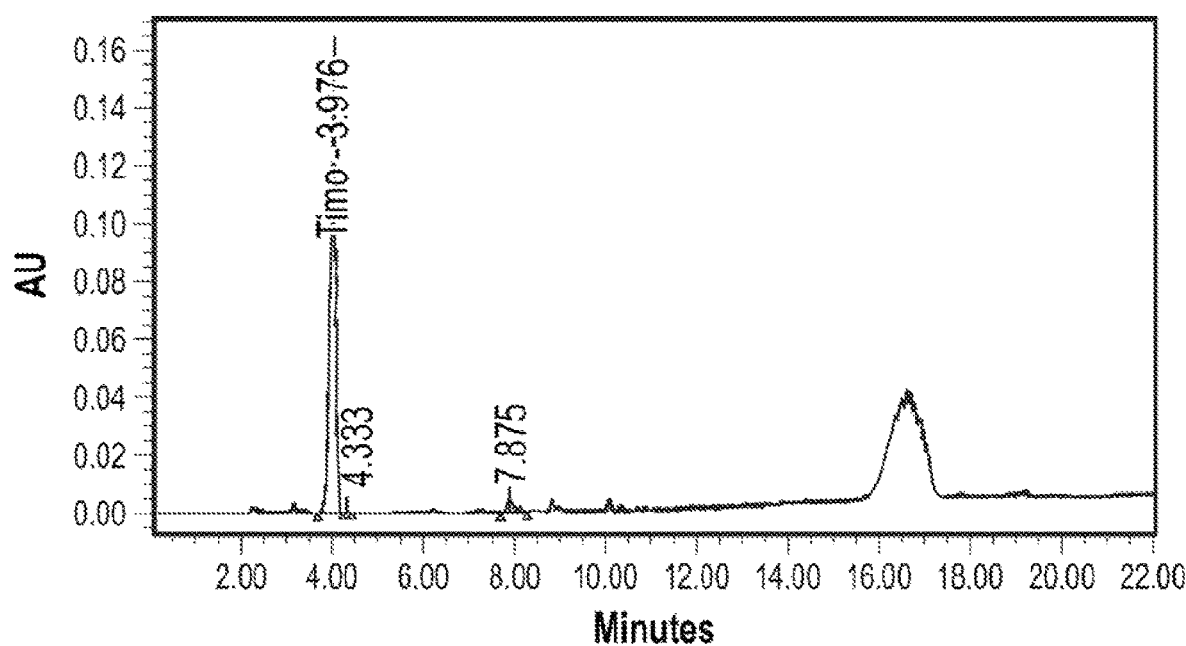
Figure 19B:
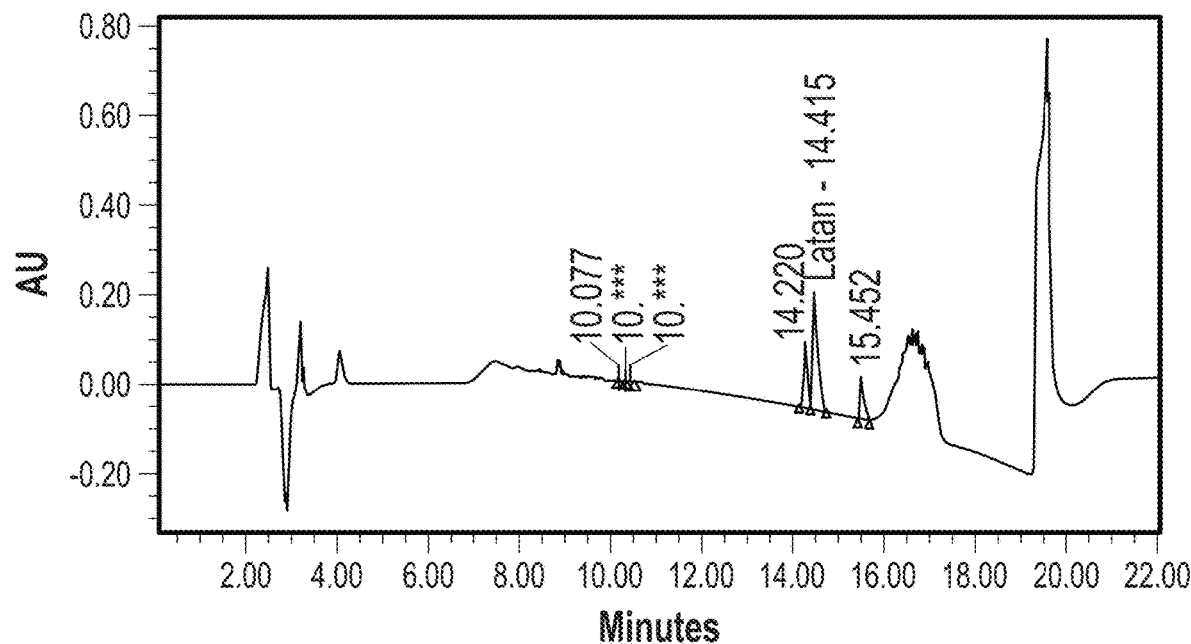

FIGS. 17, 18 and 19A-B illustrate chromatograms: FIG. 19A is a diluent chromatogram at 285 nm for Timolol Maleate; FIG. 19B is a diluent chromatogram at 210 nm for Latanoprost; FIG. 19C is a typical sample chromatogram at 285 nm for Timolol Maleate; FIG. 19D is a typical sample chromatogram at 210 for Latanoprost.

Examples of Release Profiles

Two latanoprost plugs were loaded with either 280 micrograms of latanoprost or 1000 micrograms, where the plugs had the dimensions: diameter was 0.9 mm and length was 3 mm. For the plug loaded with 280 micrograms of latanoprost, about 150-200 micrograms was released within 170 days at rates from 5 micrograms/day to 0.5 micrograms/day. For the plug loaded with 1000 micrograms of latanoprost, about 300-350 micrograms of latanoprost was released within 110 days at rates from 10 micrograms/day to 2 micrograms/day. For the 1000 microgram loaded plugs, the plugs can be coated to release 70-80 micrograms within 110 days at rates of 2-0.5 micrograms/day. FIGS. 1B and 1C illustrate the latanoprost plug and the timolol plug, respectively. The plug can contain between 0-35% Latanoprost w/w (e.g., 0.1, 1, 2, 3, 4, 5, 6, 7, 8, 9, 10, etc.). The plug can contain between 0-35% Timolol w/w (e.g., 0.1, 1, 2, 3, 4, 5, 6, 7, 8, 9, 10, etc.).

A plug loaded with 400 micrograms Timolol and 250 micrograms Latanoprost, where the plug has dimensions of a diameter measuring 0.9 mm and a length measuring 3 mm, the release profile was about 300 micrograms of timolol and about 160 micrograms of Latanoprost within 30 days at rates of 50-5 micrograms/day for TM and 10 to 5 micrograms/day for latanoprost.

Example: Particulate Preparation

A solvent mixture was prepared, including THF:Ethanol in a 1:1 (w/w) ratio. First, Latanoprost is mixed with these solvents and then Latanoprost is added to fumed silica (Sigma Aldrich 0.2-0.3 micrometers as the average particle size, CAS 112945-52-5). For example: FS60 (60% drug, e.g., Latanoprost): 0.3 g FS+(0.2 g Latanoprost+5 g solvent), where FS is fumed silica. The mixture is then dried at room temperature for about 2 days. The percent moisture (relative humidity, "RH") can be between 30-70%.

Example: Composite Matrix

To prepare an epoxy solution, 1 g Part A (Bisphenol A) is added to 0.25 g Part B (Reactive diluent; Epo-tek 301). Kaolin, FS60, and epoxy are mixed, and later molded into a shape (e.g., a punctual plug shape). Then, the mixture is cured at room temperature for 2 days. In an example, the composite (36% drug, e.g., Latanoprost): 0.2 g Kolin+0.2 g epoxy+0.6 g FS60 is mixed, molded into a shape, and cured.

Example: Dispersed Composite Matrix in Polyurethane

To prepare an epoxy solution, 1 g Part A is added to 0.25 g Part B. Kaolin (Sigma, CAS 1332-58-7), FS60, and Epoxy are mixed and this mixture is cured at room temperature for 2 days. The composite is ground and vacuum dried for 24 hours. The polyurethane solution is prepared using 4 g Part A and 1 g Part B (polyurethane steralloy 2781, Hapco Inc.). The Polyurethane is mixed with composite powder, and then molded into a shape (e.g., a punctual plug). For example, a plug having 14% drug (e.g., Latanoprost) would be generated by adding a composite powder to polyurethane to yield 0.5 g (composite powder) and 0.75 g polyurethane.

Example: Two Active Agents Dispersed in Polyurethane

Part 1: Particulate Preparation

The particulate was prepared by mixing solvents, e.g., tetrahydrofuran (THF):ethanol in a 1:1 (w/w) ratio. Then, Latanoprost was mixed with the solvents and added to fumed silica. Timolol (TML) was then mixed with the solvents and added to fumed silica. For example, FS60TML (60% Timolol drug): 0.3 g FS+(0.2 g TML+5 g solvent), then FS60LTP (60% Latanoprost drug): 0.3 g FS+(0.2 g Latanoprost drug+5 g solvent), and then the mixture is dried for two days at room temperature (relative humidity is between 30-70%).

Part 2: Composite Matrix

The epoxy solution was prepared using 1 g Part A and 0.25 g Part B. Kaolin, FS60LTP, FS60TML, and epoxy were mixed and then cured at room temperature for 2 days at a relative humidity of between 30-70%. The composite was then ground, creating <10 micrometer sized particles (e.g., but not limited to, between 0.001, 0.01, 0.1, 1, 2, 3 micrometers, etc.), and vacuum dried. The polyurethane solution was then prepared using 4 g Part A and 1 g Part B, and the polyurethane preparation was then mixed with the composite powder and subsequently molded into a shape, e.g., a punctual plug.

In another example of generating a composite matrix, the epoxy solution was prepared using 1 g Part A and 0.25 g Part B. Kaolin, FS60LTP, FA60TML, and epoxy were then mixed and this mixture was cured at room temperature for two days. The composite was ground into powder, creating <10 micrometer sized particles (e.g., but not limited to, between 0.001, 0.01, 0.1, 1, 2, 3 micrometers, etc.) and subsequently vacuum dried. For example, a composite matrix formulation was generated using 0.6 g FS60TML, 0.4 g FS60LTP, 0.33 g Kaolin and 0.4 g Epoxy, yielding a final dose in composition having 20% Timolol and 13.5% Latanoprost.

Part 3: Dispersed Composite Powder in Polyurethane

The polyurethane solution was prepared using 4 g Part A and 1 g Part B. This preparation was then mixed with composite powder and molded. For example, the plug with 8.1% Timolol and 5.4% Latanoprost was generated using 0.35 g (Timolol and Latanoprost) composite powder and polyurethane, and then molded into a shape, e.g., a punctual plug. For example, a plug having 8.1% Timolol and 5.4% Latanoprost would be generated using 0.35 g (20.3% Timolol and 13.5% Latanoprost composite powder) and 0.53 g polyurethane.

Example: In Vitro Studies

Figure 20:
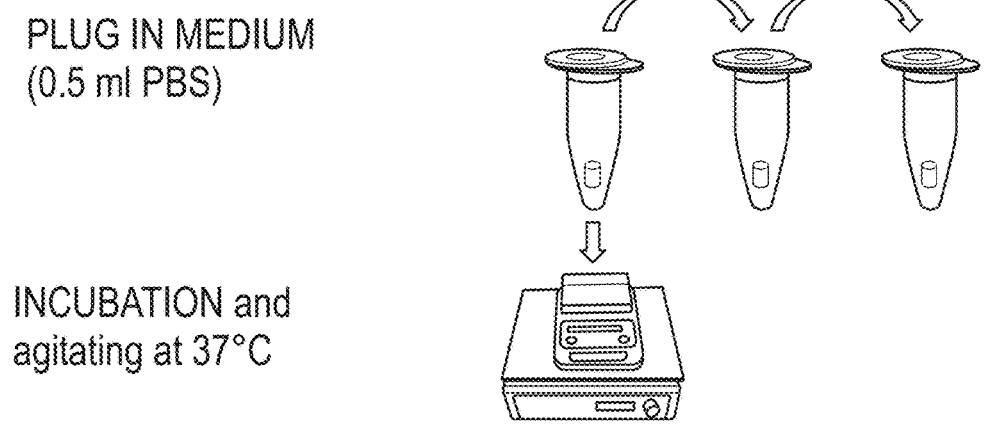
FIG. 20 illustrates an embodiment of the method of the present invention.
Figure 21:
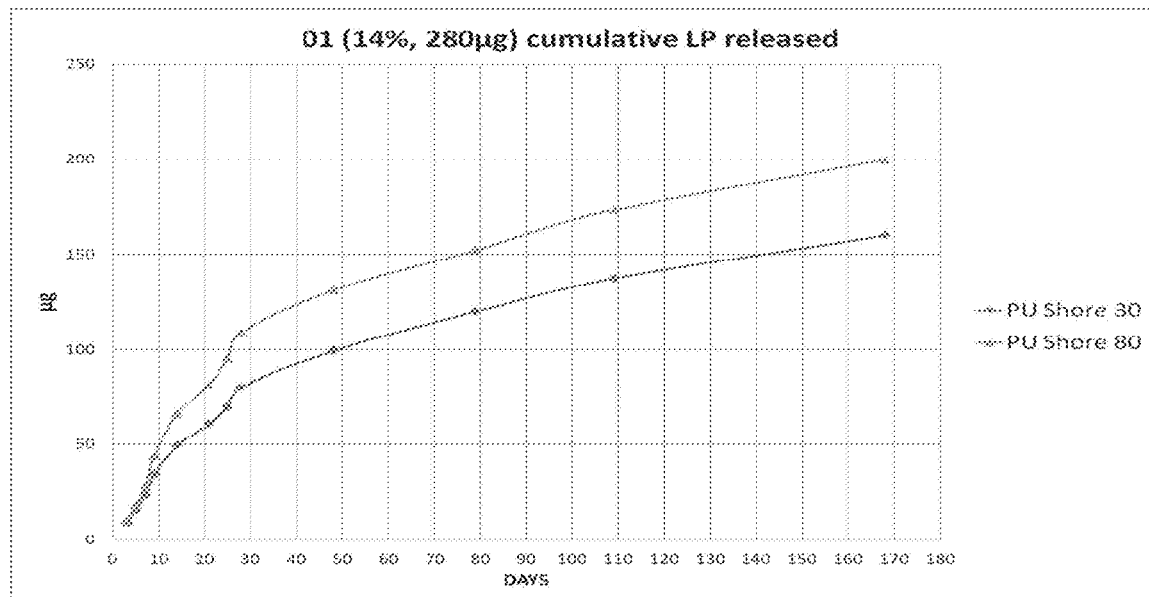
FIGS. 21 and 22 illustrate graphs of release profiles of embodiments of the composition of the present invention.
Figure 22:
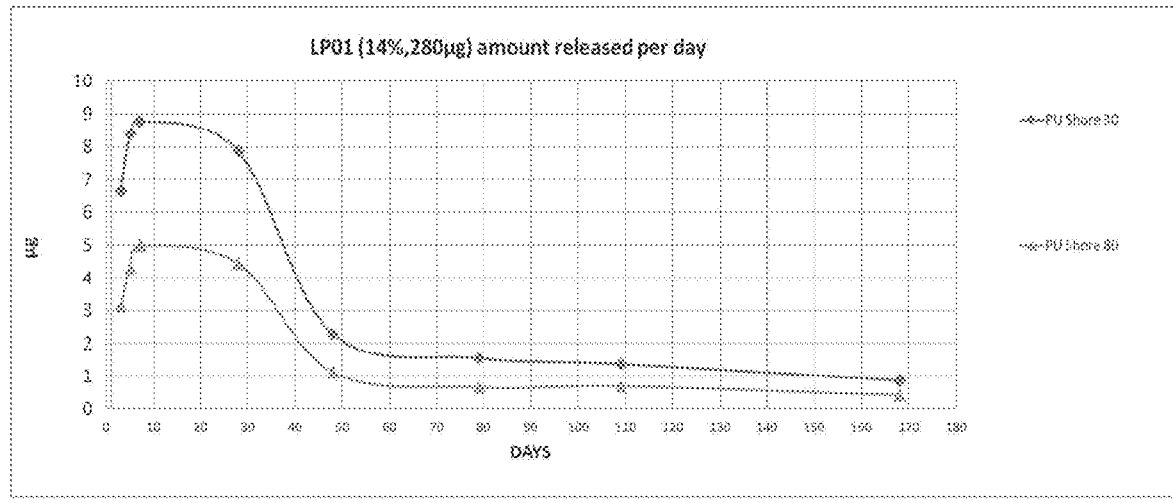

The general protocol for the analytics study design was as follows: (1) preparing the following solution: phosphate buffered saline (10×PBS)+benzalkonium chloride(BAK) (0.005%)+Triton-X (0.1%), and adding 0.5 mL of this solution into 1.5 mL vials. The plugs were weighed (about 5 mg/plug), and then each plug was placed into vials (i.e., one plug per vial) containing solution. The vials containing the plugs were then agitated in a heater at 37° C. at 30 rpm. The samples were taken according to time intervals by removing the plug sample from the vial and putting vials in a refrigerator at 4 degrees C. A figure describing these steps is shown as FIG. 20. FIG. 21 is a graph showing 6 months release of Latanoprost. FIG. 22 is a graph showing release of Latanoprost per day.

Figure 23:
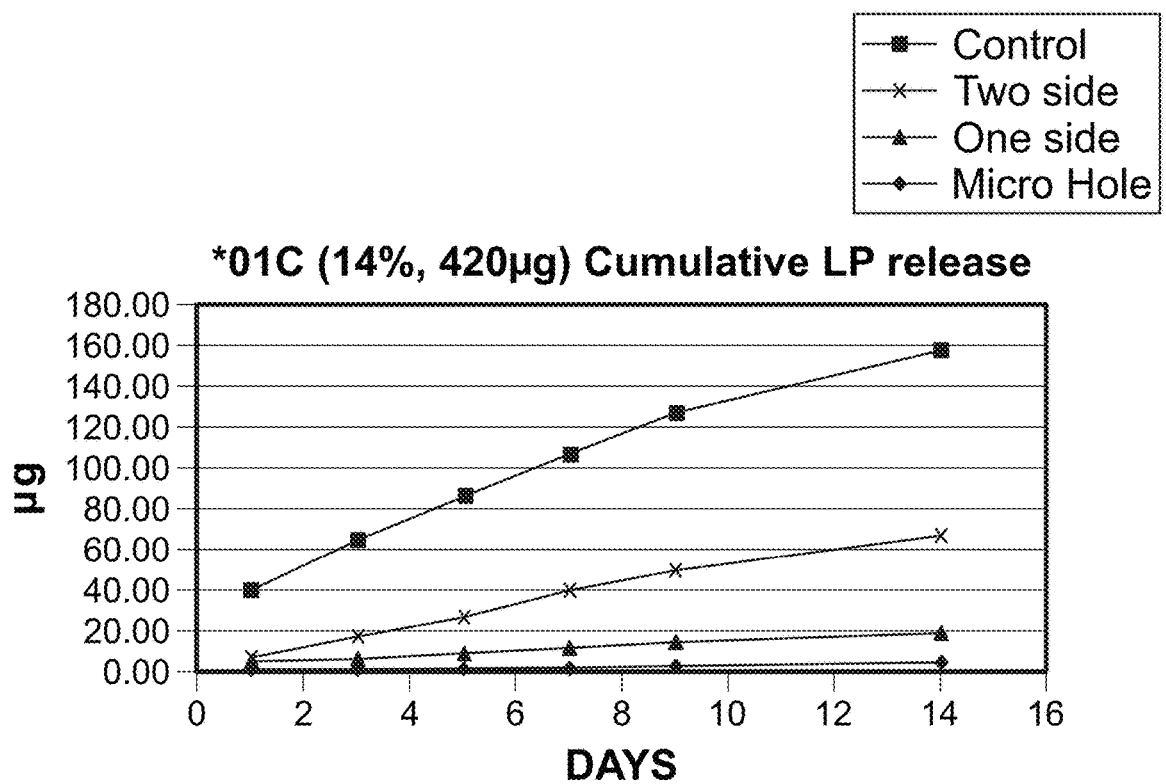
FIGS. 23-27 illustrate graphs of release profiles of embodiments of the composition of the present invention.

FIG. 23 illustrates the cumulative Latanoprost release of a parylene coated punctual plug (e.g., but not limited to, where the microhole is between 0.5-5.0 microns (e.g., but not limited to, 0.5 microns, 0.6 microns, 0.7 microns, etc.)), where the parylene coating measures between 0.2-5.0 microns in thickness (e.g., but not limited to, 0.2 microns, 0.3 microns, 0.4 microns, 0.5 microns, 0.6 microns, etc.)

Figure 24:
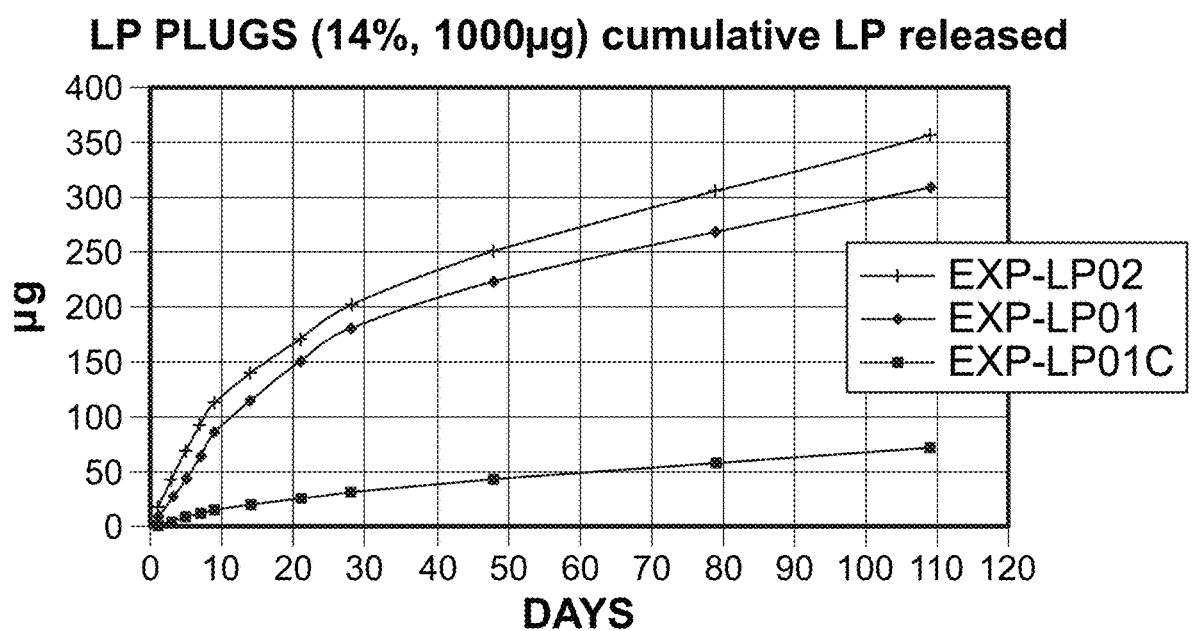

FIG. 24 illustrates a three month release profile, comparing EXP-LP02=Only composite (without polyurethane), EXP-LP01=Composite powder in polyurethane, and EXP-LP01C=Coated Composite powder in polyurethane.

Figure 25:
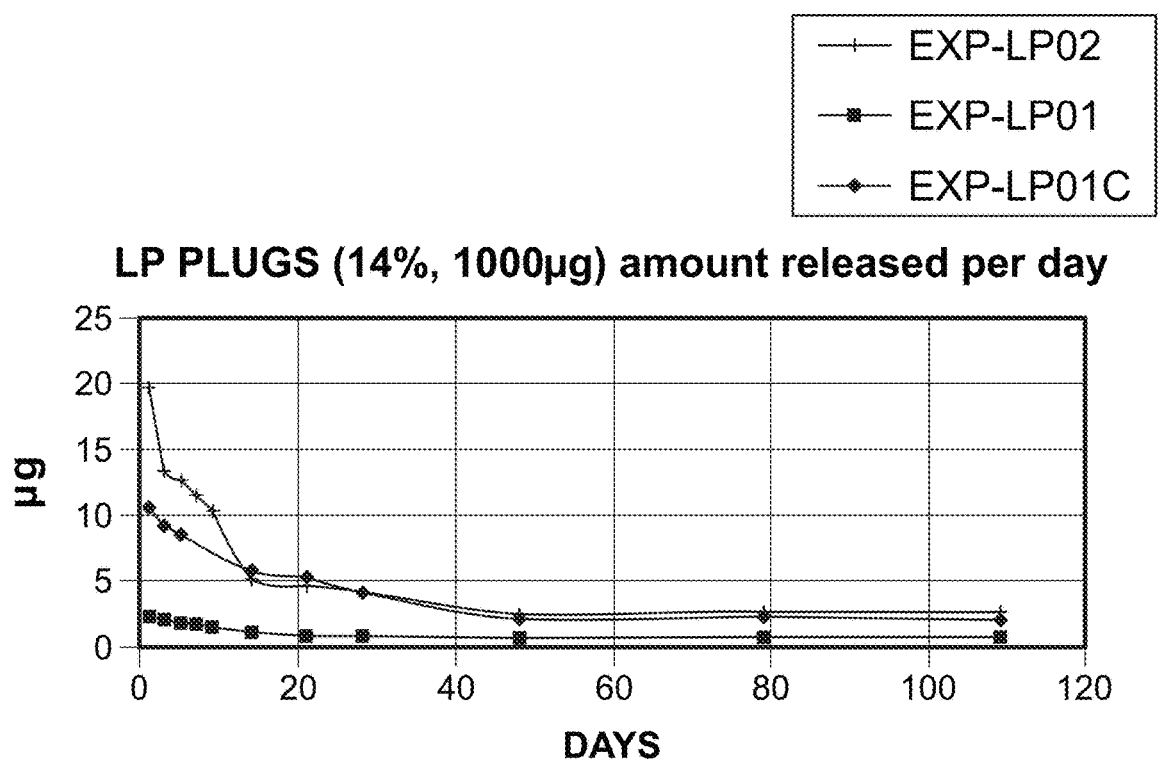

Each EXP graph made of duplicate), LP-02, and LP01C experiments. FIG. 25 illustrates a three month release profile, showing the amount of Latanoprost released per day.

Figure 26:
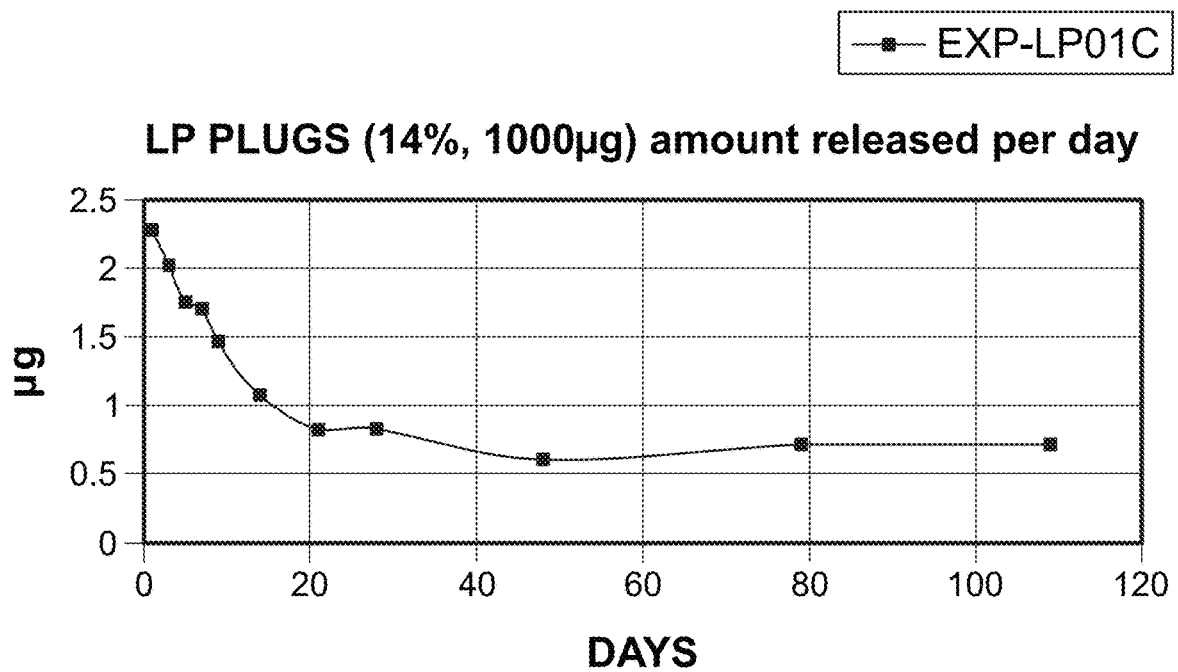

FIG. 26 illustrates the cumulative drug released, e.g., Timolol (TML) and Latanoprost (LP), from the punctual plugs.

Figure 27:
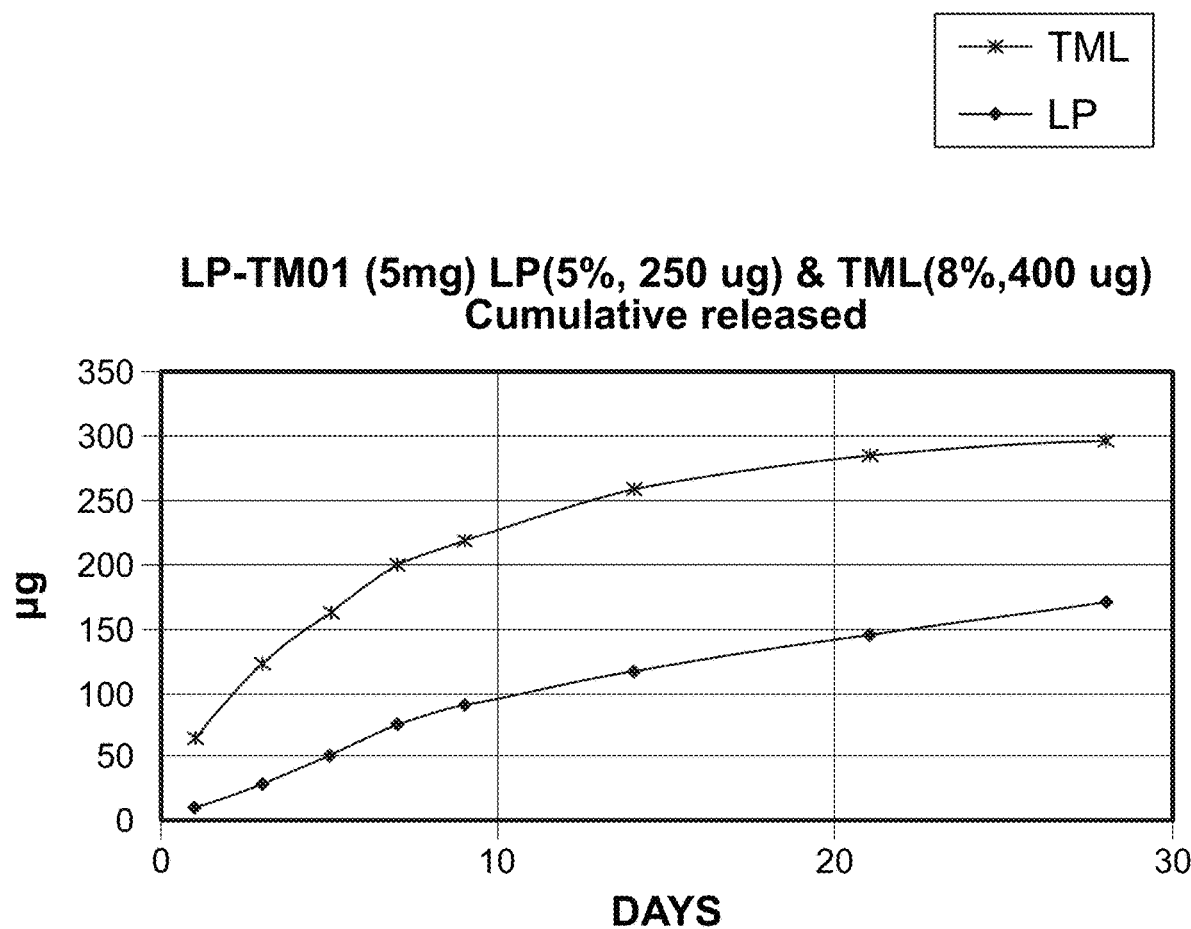

FIG. 27 illustrates the amount of LP(5%) and TML(8%) released from a 5 mg punctual plug per day.

Example: Comparison of Latanoprost Composite, Latanoprost-Polyurethane and Parylene Coated Plugs Three types of punctual plug were prepared for an HPLC analytics test: (1) polyurethane/fused silica with composite powder containing drug (PU:FS60) at a ratio of 60:40, with the final drug content of 14%; (2) polyurethane/fused silica (PU:FS60) with composite powder containing drug and having a parylene coating with a final drug content of 14%; and (3) Only composite (FS60+Kaolin+Epoxy) having a final drug content of 14.62%.

Reagents:
Kaolin USP Sigma C.N k1512-500G, Lot. No
Hexan, ANHYDROUS, 95%, Sigma C.N 296090-1L, Lot. No
Silica, Fumed Avg. Part. Size. 0.2-0.3 Sigma C.N S50S-500G, Lot. No
EPOXY EPO-TEK Part A Batch PB116550 date of Exp 03.2015
EPOXY EPO-TEK Part BBatch PB116544 date of Exp 03.2015
THF, tetrahydrofuran CAS Number 109-99-9
Ethyl alcohol (Ethanol) 96% CAS 64-17-5
Latanoprost CAS 1302-9-82-4 Lot PG01-20140101 Mfg date May 1, 2014 Manufacturer codes—R-0673.14, 584-03
Polyurethane HAPCO-Steralloy™ FDG—Elastomeric, No. 2781 (4A: B)
Triton™ X-100, SIGMA-ALDRICH 5 ml—CAS Number 9002-93-1

Equipment:
Kern ABJ 80-4NM Analytical balance 0.1 mg
Freezer EL2280 Electra.
Mini dry bath-Minlib-100, Miulab instruments, Lumitron ltd
Mortar and pestle
Orbital Shaker—SSM1, Stuart—England
Desiccators (Pre-dried in oven for 2 hours, 200° C.) 334278 SIGMA-ALDRICH, Molecular sieves, 3 Å, pellets, 3.2 mm.

Additional Materials Used:
Molding block—pressing and molding the composite with PU into cylinder shape
Aluminum foil
Plastic cups Sample Preparation Methodology:
Only Composite Samples (Type 3):
1. Particulate Preparation (FS60) for Only Composite Sample
6 ml solvents mixture of THF:Ethanol 1:1 (w/w)
First Latanoprost mixing with solvents and then adding FS
FS60: 0.29 g FS+(0.44 g LP+5 g solvent)→Drying 2 days RT
2. Matrix Preparation (See Table 4.1 Below for Amounts)
EPOXY solution preparation→1 g Part A and 0.25 g Part B
Kaolin+FS60+Epoxy→Dried at Room Temp for 2 days
LP14.5% Composite plug to 5 mg sample (cylinder shape)

TABLE 4.1

| Matrix | FS60 (gr) | KAOLIN (gr) | EPOXY (gr) | Final LP |
|---|---|---|---|---|
| LP14.5% Composite | 0.054 | 0.0824 | 0.0863 | 14.62% |

PU+Composite Powder (Type 1 and Type 2)
1. Particulate Preparation (FS60) for PU+Composite Powder
10 ml solvents mixture of THF:Ethanol 1:1 (w/w)
First Latanoprost mixing with solvents and then adding FS
FS60: 0.6648 g FS+(1 g LP+10 g solvent) 4 Drying 2 days RT
2. Matrix Preparation (See Table 4.2 Below for Amounts)
EPOXY solution preparation→1 g Part A and 0.25 g Part B
Kaolin+FS60+Epoxy 4 Dried at Room Temp for 2 days
Grinding dried LP-FS60 using mortar.
Drying grinded LP-FS60 using desiccators for 3 days.

TABLE 4.2

| Matrix | Composite FS60 (gr) | KAOLIN (gr) | EPOXY (gr) | Final LP |
|---|---|---|---|---|
| LP35.5%-Composite (for PU) | 1.203 | 0.421 | 0.409 | 35.53% |

3. PU Sample Preparation:
Polyurethane HAPCO 2781 solution preparation→4 g Part A and 1 g Part B.

Samples:

| Plug Sample (PU | LP35.5%-Composite-15-03-2015 (gr) | PU (gr) | Final LP % |
|---|---|---|---|
| LP14% | 0.509 | 0.78 | 14.0% |

Solution preparation for the incubation of the plugs (PBS+BAK+Triton)

Weighting BAK and TRITON (see table for amounts)

Adding PBS

| TRITON % | TRITON (gr) | BAK % | BAK (gr) | PBS ml |
|---|---|---|---|---|
| 0.1006 | 0.0403 | 0.0056 | 0.0023 | 40.00 |

Samples:
Preparing controls according to the table
Adding 0.5 ml gr solution to 1.5 vials
Putting samples into vials
Putting vials into heater at 37 degrees C.
Putting heater onto agitator on 30 RPM
Remove samples according to "sink condition method"
Sample

| | SAMPLES | Days at 37 in PBS + BAK + Triton | Composite Weight 5 mg | PBS + BAK (0.005%) + TRITON (0.1%) 0.5 g | PLUG DESIGN |
|---|---|---|---|---|---|
| | NEXTAR RUN 9 | | | | |
| 10-1 | LP14-0315-1W-CO1 | 1 | 5.71 | 0.5331 | ONLY COMPOSITE |
| 10-2 | LP14-0315-3W-CO1 | 3 | 5.71 | 0.5339 | ONLY COMPOSITE |
| 10-3 | LP14-0315-5W-CO1 | 5 | 5.71 | 0.5318 | ONLY COMPOSITE |
| 10-4 | LP14-0315-7W-CO1 | 7 | 5.71 | 0.5336 | ONLY COMPOSITE |
| 10-5 | LP14-0315-9W-CO1 | 9 | 5.71 | 0.5343 | ONLY COMPOSITE |
| 10-6 | LP14-0315-14W-CO1 | 14 | 5.71 | 0.5345 | ONLY COMPOSITE |
| 10-7 | LP14-0315-21W-CO1 | 21 | 5.71 | 0.5331 | ONLY COMPOSITE |
| 10-8 | LP14-0315-28W-CO1 | 28 | 5.71 | 0.5315 | ONLY COMPOSITE |
| 10-9 | LP14-0315-48W-CO1 | 48 | 5.71 | 0.5290 | ONLY COMPOSITE |
| 10-10 | LP14-0315-79W-CO1 | 79 | 5.71 | 0.5341 | ONLY COMPOSITE |
| 10-11 | LP14-0315-109W-CO1 | 109 | 5.71 | 0.5300 | ONLY COMPOSITE |
| 10-12 | LP14-0315-1W-CO2 | 1 | 5.81 | 0.5320 | ONLY COMPOSITE |
| 10-13 | LP14-0315-3W-CO2 | 3 | 5.81 | 0.5319 | ONLY COMPOSITE |
| 10-14 | LP14-0315-5W-CO2 | 5 | 5.81 | 0.5293 | ONLY COMPOSITE |
| 10-15 | LP14-0315-7W-CO2 | 7 | 5.81 | 0.5187 | ONLY COMPOSITE |
| 10-16 | LP14-0315-9W-CO2 | 9 | 5.81 | 0.5191 | ONLY COMPOSITE |
| 10-17 | LP14-0315-14W-CO2 | 14 | 5.81 | 0.5264 | ONLY COMPOSITE |
| 10-18 | LP14-0315-21W-CO2 | 21 | 5.81 | 0.5140 | ONLY COMPOSITE |
| 10-19 | LP14-0315-28W-CO2 | 28 | 5.81 | 0.5099 | ONLY COMPOSITE |
| 10-20 | LP14-0315-48W-CO2 | 48 | 5.81 | 0.5177 | ONLY COMPOSITE |
| 10-21 | LP14-0315-79W-CO2 | 79 | 5.81 | 0.5078 | ONLY COMPOSITE |
| 10-22 | LP14-0315-109W-CO2 | 109 | 5.81 | 0.5124 | ONLY COMPOSITE |
| 10-23 | LP14-0315-1W-P1 | 1 | 4.80 | 0.5080 | POWDER with PU |
| 10-24 | LP14-0315-3W-P1 | 3 | 4.80 | 0.5158 | POWDER with PU |
| 10-25 | LP14-0315-5W-P1 | 5 | 4.80 | 0.5138 | POWDER with PU |
| 10-26 | LP14-0315-7W-P1 | 7 | 4.80 | 0.5132 | POWDER with PU |
| 10-27 | LP14-0315-9W-P1 | 9 | 4.80 | 0.5146 | POWDER with PU |
| 10-28 | LP14-0315-14W-P1 | 14 | 4.80 | 0.5007 | POWDER with PU |
| 10-29 | LP14-0315-21W-P1 | 21 | 4.80 | 0.5203 | POWDER with PU |
| 10-30 | LP14-0315-28W-P1 | 28 | 4.80 | 0.5122 | POWDER with PU |
| 10-31 | LP14-0315-48W-P1 | 48 | 4.80 | 0.5217 | POWDER with PU |
| 10-32 | LP14-0315-79W-P1 | 79 | 4.80 | 0.5150 | POWDER with PU |
| 10-33 | LP14-0315-109W-P1 | 109 | 4.80 | 0.5230 | POWDER with PU |
| 10-34 | LP14-0315-1W-P2 | 1 | 5.15 | 0.5232 | POWDER with PU |
| 10-35 | LP14-0315-3W-P2 | 3 | 5.15 | 0.5211 | POWDER with PU |
| 10-36 | LP14-0315-5W-P2 | 5 | 5.15 | 0.5195 | POWDER with PU |
| 10-37 | LP14-0315-7W-P2 | 7 | 5.15 | 0.5261 | POWDER with PU |
| 10-38 | LP14-0315-9W-P2 | 9 | 5.15 | 0.5206 | POWDER with PU |
| 10-39 | LP14-0315-14W-P2 | 14 | 5.15 | 0.5151 | POWDER with PU |
| 10-40 | LP14-0315-21W-P2 | 21 | 5.15 | 0.5204 | POWDER with PU |
| 10-41 | LP14-0315-28W-P2 | 28 | 5.15 | 0.5192 | POWDER with PU |
| 10-42 | LP14-0315-48W-P2 | 48 | 5.15 | 0.5158 | POWDER with PU |
| 10-43 | LP14-0315-79W-P2 | 79 | 5.15 | 0.5197 | POWDER with PU |
| 10-44 | LP14-0315-109W-P2 | 109 | 5.15 | 0.5191 | POWDER with PU |
| 9-1 | LP14-0315-1W-PY1 | 1 | 4.46 | 0.5303 | COATED POWDER with PU |
| 9-2 | LP14-0315-3W-PY1 | 3 | 4.46 | 0.5320 | COATED POWDER with PU |
| 9-3 | LP14-0315-5W-PY1 | 5 | 4.46 | 0.5309 | COATED POWDER with PU |

|  | SAMPLES | Days at 37 | Composite Weight | PBS + BAK (0.005%) + TRITON (0.1%) | PLUG DESIGN |
|---|---|---|---|---|---|
| 9-4 | LP14-0315-7W-PY1 | 7 | 4.46 | 0.5306 | COATED POWDER with PU |
| 9-6 | LP14-0315-9W-PY1 | 9 | 4.46 | 0.5317 | COATED POWDER with PU |
| 9-6 | LP14-0315-14W-PY1 | 14 | 4.46 | 0.5381 | COATED POWDER with PU |
| 9-7 | LP14-0315-21W-PY1 | 21 | 4.46 | 0.5342 | COATED POWDER with PU |
| 9-8 | LP14-0315-28W-PY1 | 28 | 4.46 | 0.5366 | COATED POWDER with PU |
| 9-9 | LP14-0315-48W-PY1 | 48 | 4.46 | 0.5357 | COATED POWDER with PU |
| 9-10 | LP14-0315-79W-PY1 | 79 | 4.46 | 0.5366 | COATED POWDER with PU |
| 9-11 | LP14-0315-109W-PY1 | 109 | 4.46 | 0.5316 | COATED POWDER with PU |
| 9-12 | LP14-0315-1W-PY2 | 1 | 4.23 | 0.5367 | COATED POWDER with PU |
| 9-13 | LP14-0315-3W-PY2 | 3 | 4.23 | 0.5352 | COATED POWDER with PU |
| 9-14 | LP14-0315-5W-PY2 | 5 | 4.23 | 0.5303 | COATED POWDER with PU |
| 9-15 | LP14-0315-7W-PY2 | 7 | 4.23 | 0.5320 | COATED POWDER with PU |
| 9-16 | LP14-0315-9W-PY2 | 9 | 4.23 | 0.5325 | COATED POWDER with PU |
| 9-17 | LP14-0315-14W-PY2 | 14 | 4.23 | 0.5337 | COATED POWDER with PU |
| 9-18 | LP14-0315-21W-PY2 | 21 | 4.23 | 0.5322 | COATED POWDER with PU |
| 9-19 | LP14-0315-28W-PY2 | 28 | 4.23 | 0.5305 | COATED POWDER with PU |
| 9-20 | LP14-0315-48W-PY2 | 48 | 4.23 | 0.5297 | COATED POWDER with PU |
| 9-21 | LP14-0315-79W-PY2 | 79 | 4.23 | 0.5339 | COATED POWDER with PU |
| 9-22 | LP14-0315-109W-PY2 | 109 | 4.23 | 0.5388 | COATED POWDER with PU |

Example: Sample Testing of Polyurethane Coated Plugs

Plugs tested: Polyurethane:FS60 (60% Fused Silica:40% Latanoprost); final drug content is 14.4%. Samples were incubated at 37 degrees Celsius for varying time periods to determine the time effect of Latanoprost release profile from the sample into the PBS solution.

Reagents and Equipment:

Reagents
- Kaolin USP Sigma C.N k1512-500G,
- Hexan, ANHYDROUS, 95%, Sigma C.N 296090-1L,
- Silica, Fumed Avg. Part. Size. 0.2-0.3 Sigma C.N 55505-500G,
- EPDXY EPO-TEK Part A Batch PB046370
- EPDXY EPO-TEK Part B Batch PB046149
- Toluene Sigma CAS 108-88-3
- THF, tetrahydrofuran CAS Number 109-99-9
- Ethyl alcohol (Ethanol) 96% CAS 64-17-5
- Latanoprost CAS 1302-9-82-4 Lot PG01-20140101
- Manufacturer codes—R-0673.14, 584-03
- Triton™ X-100, SIGMA-ALDRICH 5 ml—CAS Number 9002-93-1
- Polyurethane PMC780 DRY shore80 2A:1B (not medical PU)

Equipment
- Kern ABJ 80-4NM Analytical balance 0.1 mg
- Freezer EL2280 Electra.
- Mini dry bath—Miniib-100, Miulab instruments, Lumitron ltd
- Mortar and pestle
- Orbital Shaker—SSM1, Stuart—England
- Desiccators (Pre-dried in oven for 2 hours, 200° C.) 334278 SIGMA-ALDRICH, Molecular sieves, 3 Å, pellets, 3.2 mm.

Other Materials
- Molding block—pressing and molding the composite with PU into cylinder shape
- Aluminium foil
- Plastic cups Sample Preparation Methodology:

Particulate Preparation (FS60) LP-FS60
- 6 ml solvents mixture of THF:Ethanol 1:1 (w/w)
- First Latanoprost mixing with solvents and then adding FS
- FS60: 0.2 g FS+(0.3 g LP+5 g solvent)→Drying 2 days RT
- FS with 5% TRITON (1 gr FS+0.053 g TRITON+10 g Ethanol)

Matrix Preparation (See Tables 4.2 for Amounts)
- EPDXY solution preparation→1 g Part A and 0.25 g Part B
- Kaolin+FS60+Epoxy→Dried at Room Temp for 2 days
- Grinding dried LP-FS60 using mortar and pestle.
- Drying grinded LP-FS60 using desiccators for 3 days.

Composite

| Matrix | FS60 (gr) | KAOLIN (gr) | EPOXY (gr) | Final LP |
|---|---|---|---|---|
| LP36%-Composite | 0.34 | 0.11 | 0.11 | 36.0% |

Sample Preparation (See Table Below for Amounts)

Polyurethane PMC780 solution preparation→2 g Part A and 1 g Part B

Samples

| Sample | Company | Type | Shore | Parylene Coating | Butvar Coating | Exposure degree |
|---|---|---|---|---|---|---|
| E | Smooth-on | PMC 780 | 80 | NO | NO | CONTROL |
| F | Smooth-on | PMC 780 | 80 | YES | NO | Micro hole |
| G | Smooth-on | PMC 780 | 80 | YES | NO | One side |
| H | Smooth-on | PMC 780 | 80 | NO | YES | NO |
| I | Smooth-on | PMC 780 | 80 | YES | NO | Two sides |

Final Samples

| Plug Sample | LP36%-Composite-09-2014 (gr) | PU (gr) | Final LP % |
|---|---|---|---|
| LP14% | 0.055 | 0.085 | 14% |

Figure 28A:
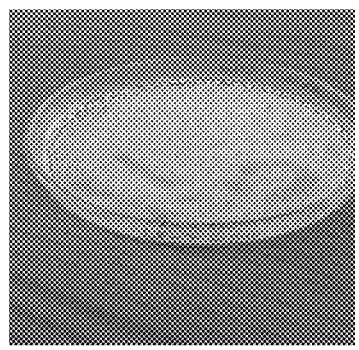
FIGS. 28A and 28B are photographs of embodiments of the composition of the present invention.
Figure 28B:
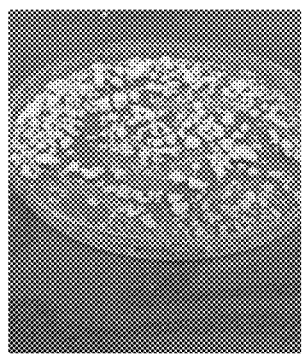
Figure 29:
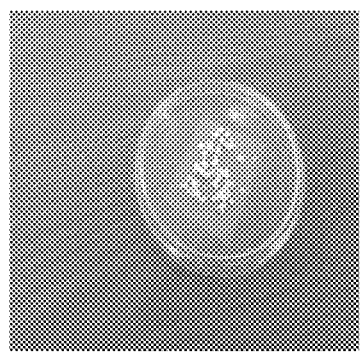
FIG. 29 is a photograph of a composite sample of an embodiment of the composition of the present invention.

Solution Preparation
  0.01M PBS+0.005% BAK+0.1% TRITON X-100
Table 4.5 Samples
2. SAMPLES PREPARATION: FS60 (Particulate Preparation)
  Weighing 3 g HFE+3 g Ethanol=6 ml solvents mixture
  Weighing 0.3 g LP
  Mixing gently LP with 2 g solvents mixture using magnetic stirrer
  Weighing 0.2 g FS
  Adding LP with solvents to 0.2 g FS
  Mixing gently materials using spatula to avoid air
  Keeping in RT for 2 days
  FIG. 28A shows the sample at the beginning of a 2 day incubation at
RT. FIG. 28B shows the sample after 2 days at RT.
Composite Preparation:
  Weighing FS60 and KAOLIN (see table for amounts)
  Mixing gently materials using spatula
  Adding EPDXY (Final solution A+B) (see table for amounts)
  Mixing materials using spatula
  Cutting 2 PE sheets
  Putting small composite granules (Cuscus shape)
  Staying in Refrigeration (4 Celsius) for two days
  The composite samples are shown in FIG. 29.
Final Formulation

| Etha-nol | % (X100) | 5% (X100) | FS (X100) | % drug in composite | Epoxy | Kaolin | FS concentrate |
|---|---|---|---|---|---|---|---|
| gr 0.300 Final 2.3 | Final 0.120 | gr 0.001 | gr 0.015 | 35.675 | gr 0.130 | gr 0.111 | gr 0.375 |

Figure 30:
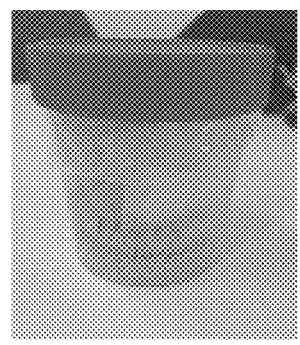
FIG. 30 illustrates desiccators used while generating embodiments of the compositions of the present invention.

Composite Milling
  Putting granules into mortar and use pestle to mill the granules to fine powder.
  Adding dried desiccators into plastic cup and adding powder to a small cup.
  FIG. 30 shows the dried desiccators placed in a plastic cup and adding powder to the 10 mL cup.
PU+Composite:
  Weighting 0.055 Composite
  Weighting part A and part B of PU
  Mixing for 5 minutes PU
  Weighting 0.085 PU
  Mixing PU and Composite into smooth paste (e.g., no particles were observed in this mixture)
  Putting the paste onto the molding block.
  Curing for 48 hr in an ambient temperature

| Plug Sample | LP36%-Composite-09-2014 (gr) | PU (gr) | Final LP % |
|---|---|---|---|
| LP14% | 0.056 | 0.086 | 14.0% |

Solution preparation (PBS+BAK+Triton)
Weighting BAK and TRITON (see table for amounts)
Adding PBS

| TRITON % | TRITON (gr) | BAK % | BAK (gr) | PBS ml |
|---|---|---|---|---|
| 0.095 | 0.0285 | 0.0060 | 0.0018 | 30.026 |

Samples
  Preparing controls according to the table
  Adding 0.5 ml gr solution to 1.5 vials
  Weighting 5 mg samples (0.005 gr)
  Putting samples into vials
  Putting vials into heater at 37 degrees C.
  Putting heater onto agitator on 30 RPM
  Remove samples according to "sink condition method" for example: Samples No. 3, 11, 19, 27 Removing composites from vial after 3 days and putting vials in the refrigerator than put the composite in new vials 1, 3, 5, 7, 9, etc. (See, e.g., FIG. 20)

| | COMPOSITE FS60 + PU | Days at 37 | Composite Weight | PBS + BAK (0.005%) + TRITON(0.1%) |
|---|---|---|---|---|
| | NEXTAR RUN 7 | in PBS + BAK + Triton | 3 mg | 0.5 g |
| 1 | Con2 (PBS + BAK + TRITON + LP) | 28 days at 4 Celcius | 3.70 | 0.516 |
| 2 | Con3 (PBS + BAK + TRITON + LP) | 28 days at 37 | 3.5 | 0.634 |
| 3 | LP14-1114-1D-E | 1 | 2.0 | 0.548 |
| 4 | LP14-1114-3D-E | 3 | 2.0 | 0.566 |
| 5 | LP14-1114-5D-E | 5 | 2.0 | 0.583 |
| 6 | LP14-1114-7D-E | 7 | 2.0 | 0.571 |
| 7 | LP14-1114-9D-E | 9 | 2.0 | 0.553 |
| 8 | LP14-1114-14D-E | 14 | 2.0 | 0.546 |
| 9 | LP14-1114-1D-F | 1 | 3.6 | 0.526 |
| 10 | LP14-1114-3D-F | 3 | 3.6 | 0.542 |
| 11 | LP14-1114-5D-F | 5 | 3.6 | 0.599 |
| 12 | LP14-1114-7D-F | 7 | 3.6 | 0.549 |
| 13 | LP14-1114-9D-F | 9 | 3.6 | 0.494 |
| 14 | LP14-1114-14D-F | 14 | 3.6 | 0.507 |
| 15 | LP14-1114-1D-G | 1 | 2.8 | 0.544 |
| 16 | LP14-1114-3D-G | 3 | 2.8 | 0.515 |
| 17 | LP14-1114-5D-G | 5 | 2.8 | 0.575 |
| 18 | LP14-1114-7D-G | 7 | 2.8 | 0.523 |
| 19 | LP14-1114-9D-G | 9 | 2.8 | 0.618 |
| 20 | LP14-1114-14D-G | 14 | 2.8 | 0.564 |
| 21 | LP14-1114-1D-H | 1 | 3.3 | 0.587 |
| 22 | LP14-1114-3D-H | 3 | 3.3 | 0.611 |
| 23 | LP14-1114-5D-H | 5 | 3.3 | 0.546 |
| 24 | LP14-1114-7D-H | 7 | 3.3 | 0.531 |
| 25 | LP14-1114-9D-H | 9 | 3.3 | 0.504 |
| 26 | LP14-1114-14D-H | 14 | 3.3 | 0.536 |
| 27 | LP14-1114-1D-I | 1 | 2.6 | 0.510 |
| 28 | LP14-1114-3D-I | 3 | 2.6 | 0.580 |
| 29 | LP14-1114-5D-I | 5 | 2.6 | 0.541 |
| 30 | LP14-1114-7D-I | 7 | 2.6 | 0.553 |
| 31 | LP14-1114-9D-I | 9 | 2.6 | 0.539 |
| 32 | LP14-1114-14D-I | 14 | 2.6 | 0.549 |

Example: Timolol and Latanoprost Composite

This example focuses on a sample containing:
PU (Hapco2781):FS60-(60% Latanoprost:40% Timolol), final Timolol content % is 8.1% and the final Latanoprost content % is 5.4%.

Reagents and Equipment:

Reagents

Kaolin USP Sigma C.N k1512-500G,
Hexan, ANHYDROUS, 95%, Sigma C.N 296090-1L
Silica, Fumed Avg. Part. Size. 0.2-0.3 Sigma C.N 55505-500G,
EPDXY EPO-TEK Part A Batch PB116550
EPDXY EPO-TEK Part B Batch PB116544
THF, tetrahydrofuran CAS Number 109-99-9
Ethyl alcohol (Ethanol) 96% CAS 64-17-5
Latanoprost CAS 1302-9-82-4 Lot PG01-20140101
Manufacturer codes—R-0673.14, 584-03 (NEORE PHARMA)
Timolol CAS 26921-17-5 Lot 140303 Mfg date 03/2014 (NEORE PHARMA)
Polyurethane HAPCO—Steralloy™ FDG—Elastomeric, No. 2781 (4A: B)
Triton™ X-100, SIGMA-ALDRICH 5 ml—CAS Number 9002-93-1

Equipment

Kern ABJ 80-4NM Analytical balance 0.1 mg
Freezer EL2280 Electra.
Mini dry bath—Miniib-100, Miulab instruments, Lumitron ltd
Mortar and pestle
Orbital Shaker—SSM1, Stuart—England
Desiccators (Pre-dried in oven for 2 hours, 200° C.) 334278 SIGMA-ALDRICH, Molecular sieves, 3 Å, pellets, 3.2 mm.

Other Materials

Molding block—pressing and molding the composite with PU into cylinder shape
Aluminum foil
Plastic cups Sample Preparation Methodology:

Particulate Preparation (FS60LTP) LP-FS60
  6 ml solvents mixture of THF:Ethanol 1:1 (w/w)
  Latanoprost mixing with solvents and then adding FS
  FS60: 0.2 g FS+(0.33 g LP+5 g solvent)→Drying 2 days RT Particulate Preparation (FS60TML) TML-FS60
  6 ml solvents mixture of THF:Ethanol 1:1 (w/w)
  Timolol mixing with solvents and then adding FS
  FS60: 0.2 g FS+(0.33 g TML+5 g solvent)→Drying 1 day RT Composite Matrix Preparation (See Table Below for Amounts)
  EPDXY solution preparation→1 g Part A and 0.25 g Part B
  Kaolin+FS60+Epoxy→Dried at Room Temp for 2 days (see table below)
  Grinding dried FS60 (for PU) using mortar.
  Drying grinded FS60 (for PU) using desiccators for 3 days.

| % drug in composite | % drug in composite | Epoxy | Kaolin | FA TOTAL | FS LTP | FS TM |
|---|---|---|---|---|---|---|
| LTP | TIM | gr | gr | | gr | gr |
| 13.53834588 | 20.3075188 | 0.44 | 0.333333333 | 1 | 0.4 | 0.5 |

Sample Preparation (See Tables 4.3 for Amounts)
  Polyurethane HAPCO 2781 solution preparation→4 g Part A and 1 g Part B were mixed together and 0.53 grams of the mixture was used for the formulation Samples

| Plug Sample | Composite powder (gr) | PU (gr) | Final TML % | Final LP % |
|---|---|---|---|---|
| LP&TML-0615 | 0.35 | 0.53 | 8.1% | 5.4% |

Solution Preparation
0.01M PBS+0.005% BAK+0.1% TRITON X-100

TABLE 4.5

Samples

| SAMPLES | Days at 37 | Composite Weight | PBS = BAK (0.005%) + TRITON(0.1%) |
|---|---|---|---|
| NEXTAR RUN 12 | In PBS + BAK + Triton | 5 mg | 0.5 g |
| LP&TML-0615-1d-P1 | 1 | 3.90 | 0.525 |
| LP&TML-0615-3d-P1 | 3 | 3.90 | 0.518 |
| LP&TML-0615-5d-P1 | 5 | 3.90 | 0.520 |
| LP&TML-0615-7d-P1 | 7 | 3.90 | 0.521 |
| LP&TML-0615-9d-P1 | 9 | 3.90 | 0.517 |
| LP&TML-0615-14d-P1 | 14 | 3.90 | 0.514 |
| LP&TML-0615-21d-P1 | 21 | 3.90 | 0.516 |
| LP&TML-0615-28d-P1 | 28 | 3.90 | 0.521 |
| LP&TML-0615-48d-P1 | 58 | 3.90 | 0.516 |
| LP&TML-0615-79d-P1 | 96 | 3.90 | 0.517 |
| LP&TML-0615-109d-P1 | 126 | 3.90 | 0.565 |
| LP&TML-0615-1d-P2 | 1 | 3.50 | 0.524 |
| LP&TML-0615-3d-P2 | 3 | 3.50 | 0.520 |
| LP&TML-0615-5d-P2 | 5 | 3.50 | 0.517 |
| LP&TML-0615-7d-P2 | 7 | 3.50 | 0.522 |
| LP&TML-0615-9d-P2 | 9 | 3.50 | 0.519 |
| LP&TML-0615-14d-P2 | 14 | 3.50 | 0.522 |
| LP&TML-0615-21d-P2 | 21 | 3.50 | 0.516 |
| LP&TML-0615-28d-P2 | 28 | 3.50 | 0.521 |

Sample Preparation

LP-FS60 (Particulate Preparation)
  Weighing 3 g HFE+3 g Ethanol=6 ml solvents mixture
  Weighing 0.2 g LP
  Mixing gently LP with 5 g solvents mixture using magnetic stirrer
  Weighing 0.3 g FS
  Adding LP with solvents to 0.3 g FS
  Mixing gently materials using spatula to avoid air
  Keeping in RT for 1 day TML-FS60 (Particulate Preparation)
  Weighing 3 g HFE+3 g Ethanol=6 ml solvents mixture
  Weighing 0.2 g TML
  Mixing gently TML with 5 g solvents mixture using magnetic stirrer
  Weighing 0.3 g FS
  Adding LP with solvents to 0.3 g FS
  Mixing gently materials using spatula to avoid air
  Keeping in RT for 1 day Composite
  Weighing FS60 and KAOLIN (as shown in table above)
  Mixing gently materials using spatula
  Adding EPDXY (Final solution A+B) (as shown in table above)
  Mixing materials using spatula
  Cutting 2 PE sheets
  Putting small composite granules (Cuscus shape)
  Staying in RT for two days
Composite Milling and PU
  Putting granules into mortar and use pestle to mill the granules to fine powder (e.g., but not limited to, <100 microns; e.g., but not limited to, 0.01 micron, 0.1 micron, 1 micron, etc.).
  Weighting 0.350 Composite powder
  Weighting part A and part B of PU
  Mixing for 5 minutes PU
  Weighting 0.53 PU
  Mixing PU and Composite into smooth paste
  Putting the paste onto the molding block.
  Curing for 48 hr (to 30/06)
Solution Preparation (PBS+BAK+Triton)
  Weighting BAK and TRITON (see table for amounts)
  Adding PBS

| TRITON % | TRITON (gr) | BAK % | BAK (gr) | PBS ml |
| --- | --- | --- | --- | --- |
| 0.1116 | 0.0447 | 0.0058 | 0.0023 | 40.00 |

Samples
  Preparing controls
  Adding 0.5 ml gr solution to 1.5 vials
  Putting samples into vials
  Putting vials into heater at 37 degrees C.
  Putting heater onto agitator on 30 RPM
  Remove samples according to "sink condition method"

In some embodiments, the present invention is a composition, including: a bulking agent including a kaolin, an absorbent material including a fumed silica, a binder including an epoxy, and a first active agent including Latanoprost. In some embodiments, the first active agent measures between 5-40% by weight (w/w). In some embodiments, the first active agent measures between 5-35% by weight (w/w). In some embodiments, the first active agent measures between 5-30% by weight (w/w). In some embodiments, the first active agent measures between 5-25% by weight (w/w). In some embodiments, the first active agent measures between 5-20% by weight (w/w). In some embodiments, the first active agent measures between 5-15% by weight (w/w). In some embodiments, the first active agent measures between 5-10% by weight (w/w). In some embodiments, the first active agent measures between 10-40% by weight (w/w). In some embodiments, the first active agent measures between 15-40% by weight (w/w). In some embodiments, the first active agent measures between 20-40% by weight (w/w). In some embodiments, the first active agent measures between 25-40% by weight (w/w). In some embodiments, the first active agent measures between 30-40% by weight (w/w). In some embodiments, the first active agent measures between 35-40% by weight (w/w). In some embodiments, the first active agent measures between 10-35% by weight (w/w). In some embodiments, the first active agent measures between 15-30% by weight (w/w). In some embodiments, the first active agent measures between 20-25% by weight (w/w). In some embodiments, the compound further includes a second active agent. In some embodiments, the second active agent is Timolol. In some embodiments, the second active agent measures between 5-40% by weight (w/w). In some embodiments, the second active agent measures between 5-35% by weight (w/w). In some embodiments, the second active agent measures between 5-30% by weight (w/w). In some embodiments, the second active agent measures between 5-25% by weight (w/w). In some embodiments, the second active agent measures between 5-20% by weight (w/w). In some embodiments, the second active agent measures between 5-15% by weight (w/w). In some embodiments, the second active agent measures between 5-10% by weight (w/w). In some embodiments, the second active agent measures between 10-40% by weight (w/w). In some embodiments, the second active agent measures between 15-40% by weight (w/w). In some embodiments, the second active agent measures between 20-40% by weight (w/w). In some embodiments, the second active agent measures between 25-40% by weight (w/w). In some embodiments, the second active agent measures between 30-40% by weight (w/w). In some embodiments, the second active agent measures between 35-40% by weight (w/w). In some embodiments, the second active agent measures between 10-35% by weight (w/w). In some embodiments, the second active agent measures between 15-30% by weight (w/w). In some embodiments, the second active agent measures between 20-25% by weight (w/w). In some embodiments, the composition further includes polyurethane. In some embodiments, the composition further includes a parylene coating. In some embodiments, the parylene coating measures between 2-5 micrometers (e.g., but not limited to, 2.1 micrometers, 2.2 micrometers, etc.) in thickness. In some embodiments, the composition includes a butvar coating. In some embodiments, the butvar coating measures between 2-5 micrometers (e.g., but not limited to, 2.1 micrometers, 2.2 micrometers, etc.) in thickness. In some embodiments, the composition is in the form of a punctal plug.

In some embodiments, the present invention is a method, including: administering a composition to an eye of a mammal in need thereof, where the composition releases between 0.5-10 micrograms of a first active agent per day, and where the composition includes: a bulking agent including a kaolin, an absorbent material including a fumed silica, a binder including an epoxy, and the first active agent includes Latanoprost. In some embodiments, the first active agent measures between 5-40% by weight (w/w). In some embodiments, the first active agent measures between 5-35% by weight (w/w). In some embodiments, the first active agent measures between 5-30% by weight (w/w). In some embodiments, the first active agent measures between 5-25% by weight (w/w). In some embodiments, the first active agent measures between 5-20% by weight (w/w). In some embodiments, the first active agent measures between 5-15% by weight (w/w). In some embodiments, the first active agent measures between 5-10% by weight (w/w). In some embodiments, the first active agent measures between 10-40% by weight (w/w). In some embodiments, the first active agent measures between 15-40% by weight (w/w). In some embodiments, the first active agent measures between 20-40% by weight (w/w). In some embodiments, the first active agent measures between 25-40% by weight (w/w). In some embodiments, the first active agent measures between 30-40% by weight (w/w). In some embodiments, the first active agent measures between 35-40% by weight (w/w). In some embodiments, the first active agent measures between 10-35% by weight (w/w). In some embodiments, the first active agent measures between 15-30% by weight (w/w). In some embodiments, the first active agent measures between 20-25% by weight (w/w). In some embodiments, the method includes a second active agent. In some embodiments, the second active agent is Timolol. In some embodiments, the second active agent includes between 5-40% by weight (w/w). In some embodiments, the second active agent measures between 5-35% by weight (w/w). In some embodiments, the second active agent measures between 5-30% by weight (w/w). In some embodiments, the second active agent measures between 5-25% by weight (w/w). In some embodiments, the second active agent measures between 5-20% by weight (w/w). In some embodiments, the second active agent measures between 5-15% by weight (w/w). In some embodiments, the second active agent measures between 5-10% by weight (w/w). In some embodiments, the second active agent measures between 10-40% by weight (w/w). In some embodiments, the second active agent measures between 15-40% by weight (w/w). In some embodiments, the second active agent measures between 20-40% by weight (w/w). In some embodiments, the second active agent measures between 25-40% by weight (w/w). In some embodiments, the second active agent measures between 30-40% by weight (w/w). In some embodiments, the second active agent measures between 35-40% by weight (w/w). In some embodiments, the second active agent measures between 10-35% by weight (w/w). In some embodiments, the second active agent measures between 15-30% by weight (w/w). In some embodiments, the second active agent measures between 20-25% by weight (w/w). In some embodiments, the method includes a parylene coating. In some embodiments, the parylene coating measures between 2-5 micrometers (e.g., but not limited to, 2.1 micrometers, 2.2 micrometers, etc.) in thickness. In some embodiments, the composition includes a butvar coating. In some embodiments, the butvar coating measures between 2-5 micrometers (e.g., but not limited to, 2.1 micrometers, 2.2 micrometers, etc.) in thickness. In some embodiments, the composition is in the form of a punctal plug.

In some embodiments, the composition of the present invention is a drug-delivery device comprising: a) a composite comprising the following elements: (i) particles of inert materials, where the inert materials are adsorbed with drug on surface of particles (e.g., drug bound to particles) or inside porosity (e.g., drug housed within pores); (ii) a bulking agent; (iii) an adhesive binder; or any combination thereof, and b) an optional coating on the whole or partial outer surface of the body/core; where the coating is complete/continuous or perforated, e.g., but not limited to, where the coating can be butvar and/or parylene.

In some embodiments, the present invention is a composition, including: a bulking agent including a kaolin and/or a pectin, an absorbent material including a fumed silica, a binder including an epoxy, and a first active agent including Latanoprost. In some embodiments, the first active agent measures between 5-50% by weight (w/w). In some embodiments, the first active agent measures between 5-45% by weight (w/w). In some embodiments, the first active agent measures between 5-40% by weight (w/w). In some embodiments, the first active agent measures between 5-35% by weight (w/w). In some embodiments, the first active agent measures between 5-30% by weight (w/w). In some embodiments, the first active agent measures between 5-25% by weight (w/w). In some embodiments, the first active agent measures between 5-20% by weight (w/w). In some embodiments, the first active agent measures between 5-15% by weight (w/w). In some embodiments, the first active agent measures between 5-10% by weight (w/w). In some embodiments, the first active agent measures between 10-50% by weight (w/w). In some embodiments, the first active agent measures between 15-50% by weight (w/w). In some embodiments, the first active agent measures between 20-50% by weight (w/w). In some embodiments, the first active agent measures between 25-50% by weight (w/w). In some embodiments, the first active agent measures between 30-50% by weight (w/w). In some embodiments, the first active agent measures between 35-50% by weight (w/w). In some embodiments, the first active agent measures between 40-50% by weight (w/w). In some embodiments, the first active agent measures between 45-50% by weight (w/w). In some embodiments, the first active agent measures between 10-45% by weight (w/w). In some embodiments, the first active agent measures between 15-40% by weight (w/w). In some embodiments, the first active agent measures between 20-35% by weight (w/w). In some embodiments, the first active agent measures between 20-30% by weight (w/w). In some embodiments, the compound further includes a second active agent. In some embodiments, the second active agent is Timolol. In some embodiments, the second active agent measures between 5-40% by weight (w/w). In some embodiments, the second active agent measures between 5-35% by weight (w/w). In some embodiments, the second active agent measures between 5-30% by weight (w/w). In some embodiments, the second active agent measures between 5-25% by weight (w/w). In some embodiments, the second active agent measures between 5-20% by weight (w/w). In some embodiments, the second active agent measures between 5-15% by weight (w/w). In some embodiments, the second active agent measures between 5-10% by weight (w/w). In some embodiments, the second active agent measures between 10-40% by weight (w/w). In some embodiments, the second active agent measures between 15-40% by weight (w/w). In some embodiments, the second active agent measures between 20-40% by weight (w/w). In some embodiments, the second active agent measures between 25-40% by weight (w/w). In some embodiments, the second active agent measures between 30-40% by weight (w/w). In some embodiments, the second active agent measures between 35-40% by weight (w/w). In some embodiments, the second active agent measures between 10-35% by weight (w/w). In some embodiments, the second active agent measures between 15-30% by weight (w/w). In some embodiments, the second active agent measures between 20-25% by weight (w/w). In some embodiments, the composition further includes polyurethane. In some embodiments, the composition further includes a parylene coating. In some embodiments, the parylene coating measures between 2-5 micrometers (e.g., but not limited to, 2.1 micrometers, 2.2 micrometers, etc.) in thickness. In some embodiments, the composition includes a butvar coating. In some embodiments, the butvar coating measures between 2-5 micrometers (e.g., but not limited to, 2.1 micrometers, 2.2 micrometers, etc.) in thickness. In some embodiments, the composition is in the form of a punctal plug.

In some embodiments, the present invention is a method, including: administering a composition to an eye of a mammal in need thereof, where the composition releases between 0.5-10 micrograms of a first active agent per day, and where the composition includes: a bulking agent including a kaolin, an absorbent material including a fumed silica, a binder including an epoxy, and the first active agent includes Latanoprost. In some embodiments, the first active agent measures between 5-50% by weight (w/w). In some embodiments, the first active agent measures between 5-45% by weight (w/w). In some embodiments, the first active agent measures between 5-40% by weight (w/w). In some embodiments, the first active agent measures between 5-35% by weight (w/w). In some embodiments, the first active agent measures between 5-30% by weight (w/w). In some embodiments, the first active agent measures between 5-25% by weight (w/w). In some embodiments, the first active agent measures between 5-20% by weight (w/w). In some embodiments, the first active agent measures between 5-15% by weight (w/w). In some embodiments, the first active agent measures between 5-10% by weight (w/w). In some embodiments, the first active agent measures between 10-50% by weight (w/w). In some embodiments, the first active agent measures between 15-50% by weight (w/w). In some embodiments, the first active agent measures between 20-50% by weight (w/w). In some embodiments, the first active agent measures between 25-50% by weight (w/w). In some embodiments, the first active agent measures between 30-50% by weight (w/w). In some embodiments, the first active agent measures between 35-50% by weight (w/w). In some embodiments, the first active agent measures between 40-50% by weight (w/w). In some embodiments, the first active agent measures between 45-50% by weight (w/w). In some embodiments, the first active agent measures between 10-35% by weight (w/w). In some embodiments, the first active agent measures between 10-45% by weight (w/w). In some embodiments, the first active agent measures between 15-40% by weight (w/w). In some embodiments, the first active agent measures between 20-35% by weight (w/w). In some embodiments, the first active agent measures between 25-30% by weight (w/w). In some embodiments, the method includes a second active agent. In some embodiments, the second active agent is Timolol. In some embodiments, the second active agent includes between 5-40% by weight (w/w). In some embodiments, the second active agent measures between 5-35% by weight (w/w). In some embodiments, the second active agent measures between 5-30% by weight (w/w). In some embodiments, the second active agent measures between 5-25% by weight (w/w). In some embodiments, the second active agent measures between 5-20% by weight (w/w). In some embodiments, the second active agent measures between 5-15% by weight (w/w). In some embodiments, the second active agent measures between 5-10% by weight (w/w). In some embodiments, the second active agent measures between 10-40% by weight (w/w). In some embodiments, the second active agent measures between 15-40% by weight (w/w). In some embodiments, the second active agent measures between 20-40% by weight (w/w). In some embodiments, the second active agent measures between 25-40% by weight (w/w). In some embodiments, the second active agent measures between 30-40% by weight (w/w). In some embodiments, the second active agent measures between 35-40% by weight (w/w). In some embodiments, the second active agent measures between 10-35% by weight (w/w). In some embodiments, the second active agent measures between 15-30% by weight (w/w). In some embodiments, the second active agent measures between 20-25% by weight (w/w). In some embodiments, the method includes a parylene coating. In some embodiments, the parylene coating measures between 2-5 micrometers (e.g., but not limited to, 2.1 micrometers, 2.2 micrometers, etc.) in thickness. In some embodiments, the composition includes a butvar coating. In some embodiments, the butvar coating measures between 2-5 micrometers (e.g., but not limited to, 2.1 micrometers, 2.2 micrometers, etc.) in thickness. In some embodiments, the composition is in the form of a punctal plug.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A drug delivery device, comprising:
   20-30% by weight (w/w) of a bulking agent comprising a kaolin based on the total weight of the drug delivery device,
   10-20% by weight (w/w) of an absorbent material comprising a fumed silica based on the total weight of the drug delivery device,
   a binder comprising an epoxy, and
   a first active agent comprising Latanoprost
      wherein the bulking agent, the absorbent material, the binder, and the first active agent are present in the drug delivery device as a composite,
         wherein the composite comprises the fumed silica in the form of a porous structure,
         wherein the first active agent is present at least within the porous structure,
   wherein the drug delivery device is configured to release from 0.5-10 micrograms of the first active agent per day to an eye of a mammal in need thereof, and
   wherein the drug delivery device is a punctal plug.

2. The drug delivery device of claim 1, wherein the first active agent is present in an amount of 5-40% by weight (w/w) of the drug delivery device.

3. The drug delivery device of claim 1, further comprising a second active agent, wherein the second active agent comprises Timolol.

4. The drug delivery device of claim 3, wherein the Timolol is present in an amount of 5-40% by weight (w/w) of the drug delivery device.

5. The drug delivery device of claim 1, wherein the drug delivery device further comprises polyurethane.

6. The drug delivery device of claim 1, wherein the drug delivery device further comprises a parylene coating.

7. The drug delivery device of claim 6, wherein a thickness of the parylene coating ranges from 2-5 micrometers.

8. The drug delivery device of claim 1, wherein the drug delivery device further comprises a butvar coating.

9. The drug delivery device of claim 8, wherein a thickness of the butvar coating ranges from 2-5 micrometers.

10. The drug delivery device of claim 1, wherein the binder is present in the range of 15-35% by weight (w/w) of the total weight of the drug delivery device.

11. The drug delivery device of claim 1, wherein the first active agent is further present on at least one surface of the porous structure.

12. The drug delivery device of claim 1, wherein the porous structure takes the form of an interconnected capillary network.

* * * * *